US006578571B1

(12) United States Patent
Watt

(10) Patent No.: US 6,578,571 B1
(45) Date of Patent: Jun. 17, 2003

(54) DRUG DELIVERY DEVICE AND METHODS THEREFOR

(75) Inventor: Paul M. Watt, Mt Claremont (AU)

(73) Assignee: Infamed Ltd., Leederville (AU)

( * ) Notice: Subject to any disclaimer, the term of this patent is extended or adjusted under 35 U.S.C. 154(b) by 0 days.

(21) Appl. No.: 09/294,759

(22) Filed: Apr. 19, 1999

(30) Foreign Application Priority Data

Apr. 20, 1998 (AU) .............................................. PP 3054
Jun. 10, 1998 (AU) .............................................. PP 4001
Oct. 20, 1998 (AU) .............................................. PP 6601

(51) Int. Cl.[7] .......................................... A61M 11/00
(52) U.S. Cl. ............................. 128/200.14; 120/203.12
(58) Field of Search ..................... 128/200.14, 200.23, 128/204.21, 204.23, 205.23, 203.12, 203.28, 203.14, 205.13

(56) References Cited

U.S. PATENT DOCUMENTS

| | | | | |
|---|---|---|---|---|
| 4,291,688 A | * | 9/1981 | Kistler ................... | 128/200.23 |
| 4,470,412 A | | 9/1984 | Nowacki et al. | |
| 4,484,577 A | * | 11/1984 | Sackner et al. ........ | 128/203.28 |
| 4,809,692 A | * | 3/1989 | Nowacki et al. ....... | 128/206.24 |
| 4,832,015 A | | 5/1989 | Nowacki et al. | |
| 4,984,158 A | | 1/1991 | Hillsman | |
| 5,042,467 A | | 8/1991 | Foley | |
| 5,312,281 A | * | 5/1994 | Takahashi et al. ............. | 446/25 |
| 5,363,842 A | | 11/1994 | Mishelevich et al. | |
| 5,431,154 A | | 7/1995 | Seigel et al. | |
| 5,497,765 A | | 3/1996 | Praud et al. | |
| 5,522,380 A | | 6/1996 | Dwork | |
| 5,613,489 A | | 3/1997 | Miller et al. | |
| 5,704,344 A | * | 1/1998 | Cole ...................... | 128/200.14 |
| 5,758,638 A | | 6/1998 | Kreamer | |
| 5,765,553 A | | 6/1998 | Richards et al. | |
| 5,865,172 A | * | 2/1999 | Butler et al. ........... | 128/203.12 |
| 5,937,852 A | * | 8/1999 | Butler et al. ........... | 128/203.12 |

FOREIGN PATENT DOCUMENTS

| | | |
|---|---|---|
| AU | 29969/89 | 8/1990 |
| EP | 0 514 085 A1 | 11/1992 |
| FR | 2 763 507 | 11/1998 |
| GB | 2299 512 A | 10/1996 |
| GB | 2310 607 A | 9/1997 |
| WO | WO 98/44974 | 10/1998 |

* cited by examiner

*Primary Examiner*—Aaron J. Lewis
*Assistant Examiner*—Teena Mitchell
(74) *Attorney, Agent, or Firm*—Knobbe, Martens, Olson & Bear, LLP

(57) ABSTRACT

An incentive inhaler device includes an inhalation device, at least one incentive toy coupled to the inhalation device, and at least one separator. The inhalation device has a respiration device and a connector that is linkable to a delivery device. The delivery device can deliver drugs, aerosols, powder and gas. The incentive toy is respiration driven and has at least one of a visible characteristic and an audible characteristic. The separator decouples the toy from at least one component of the inhalation device to ensure directional flow of respirational air which drives the toy. The separator can include a valve, a filter, or a baffle.

56 Claims, 8 Drawing Sheets

US 6,578,571 B1

DRUG DELIVERY DEVICE AND METHODS THEREFOR

FIELD OF THE INVENTION

The present invention relates generally to improved drug delivery devices, preferably for use by children and infants, and to methods of delivering drugs using same. More particularly, the present invention provides an incentive inhaler device comprising (i) an inhalation device comprising a mask or mouthpiece and a connector that is linkable to a drug delivery device or other device for the delivery of an aerosol, powder or gas; and (ii) one or more external visible and/or audible inhalation/exhalation-driven incentive toys, wherein each of said toys is separated from one or more components of said inhalation device (i) by one or more valves, filters or baffles to ensure directional flow of inhaled/exhaled air which drives said toys. Preferably, said valves that ensure directional air flow air are positioned within a conduit that provides for the attachment of said inhalation/exhalation-driven incentive toy(s) Replaceable filters or baffles between the mask and the toy assembly and/or between the mask and the connector or spacer may additionally provide filtration of particles or moisture in exhaled air which might otherwise contaminate the toys or the connector or spacer. Preferably, said conduit is positioned between said inhalation/exhalation mask or mouthpiece and said connector for a drug delivery device or other device for the delivery of an aerosol, powder or gas. Preferably, the modular incentive inhaler device of the present invention further includes a spacer positioned between said inhalation/exhalation mask and said connector. More preferably, the modular incentive inhaler device of the present invention further includes a spacer positioned between said inhalation/exhalation mask or mouthpiece and said conduit, or alternatively, between said conduit and said connector.

GENERAL

Those skilled in the art will be aware that the invention described herein is subject to variations and modifications other than those specifically described. It is to be understood that the invention described herein includes all such variations and modifications. The invention also includes all such steps, features, compositions and compounds referred to or indicated in this specification, individually or collectively, and any and all combinations of any two or more of said steps or features.

Throughout this specification, unless the context requires otherwise the word "comprise", and variations such as "comprises" and "comprising", will be understood to imply the inclusion of a stated integer or step or group of integers or steps but not the exclusion of any other integer or step or group of integers or steps.

BACKGROUND TO THE INVENTION

A significant problem faced by the pharmaceutical industry is the need for effective means for the delivery of drugs to infants and children, in particular drugs in the form of aerosols, powders or gases which are administered by inhalation. A suitable means for the delivery of anaesthetics, and many medicaments for the treatment of respiratory ailments such as asthma, to a patient in need of treatment, is by inhalation of the drug into the airways. To achieve the delivery of gases, powders and aerosols to patients' airways, a large number of different drug delivery means have been developed including, for example, gas-borne inhalers such as asthma pumps or Metered Dose Inhalers (MDI), dry powder inhalers, breath-activated inhalers and nebulisers.

However, therapeutic regimes for the administration of aerosols, powders or gases to infants and children are often sub-optimal, because of the difficulty which this group faces in using devices for their inhalation. The efficient delivery of air-borne drugs from standard inhalation devices requires the patient to time manual activation of a drug delivery device with inhalation of the drug released therefrom, generally by achieving a slow-flow deep inspiration and adequate breath-holding, which infants and small children often find difficult to achieve without considerable training. As a consequence, many drugs delivered from standard inhalation devices are not administered efficiently to infants and small children.

There is a clear need to foster correct breathing patterns in infants and small children who use conventional inhalation devices. The lack of guidance or an incentive or encouragement in the proper use of conventional inhalation devices, for example the incentive to breathe with a pattern of normal tidal breathing, rather than with shallow hyperventilation, is clearly a disadvantage associated with the present technology.

Moreover, small children and infants typically find standard inhalation devices frightening and, as a consequence, refuse to use them. Faced with strong resistance from children, many care-givers responsible for administering medication to children report a reluctance to offer air-borne drugs for use with standard inhalation devices on a regular basis. In addition, care-givers also report that even when attempted, the delivery of aerosol/gas medication to children is often sub-optimal because the child cries and/or forcibly removes the mask from their face before the medication is taken properly.

Inhalation devices have been described which employ some form of audio or visual warning or notification of the passage of inhaled air, to ensure that the pharmaceutical drug ejected from the drug delivery means actually reaches the patient. For example, U.S. Pat. No. 4,984,158; Australian Patent No. 620375; Australian Patent No. 618789; U.S. Pat. Nos. 5,042,467; 5,363,842; 5,431,154; 5,522,380; United Kingdom Patent Application No. 2 299 512A; U.S. Pat. No. 5,758,638; French Patent Application No. 2 763 507A, and International Patent Publication No. WO 94/44974 all describe such inhalation devices.

However, inhaler devices which merely provide for an audible or visual signal to monitor a correct breathing pattern or drug delivery do not generally utilise a signal that is both capable of simple interpretation by an infant or small child, without reference to medical personnel to determine whether or not the signal generated is appropriate, and further, comprise a signal that is sufficiently pleasant to provide an inducement for their correct use by infants and small children Accordingly, such devices do not address the significant problem of overcoming the fear which children and small infants have of medical devices or encourage this user group to use inhalation devices.

A further problem encountered with conventional signalling inhalation devices is that the device becomes contaminated through use, with residual medicament that is contained in exhaled air. Additionally, when inhalation devices are used interchangeably with different drug delivery sources or MDls to administer different chemical compounds, significant cross-contamination with the different chemical compounds may occur. Accordingly, a further object of the present invention is to provide an inhalation device that does not become easily contaminated with exhaled air/medicament mixtures and is kept cleaner than conventional signalling inhalation devices.

SUMMARY OF THE INVENTION

In work leading up to the present invention, the inventors sought to develop an inhalation device that would provide an incentive to a child or small infant user as well as overcome the drug contamination problems associated with conventional devices.

The inventors realised that the signal provided by such a device must be both pleasant and provide a positive feedback to the user, in order to provide the requisite inducement. In general, devices which provide a negative feedback rather than a positive feedback to a child user, such as those which provide a visual or audible signal only during incorrect use, will not provide the necessary inducement For example, U.S. Pat. No. 5,042,467 describes a medication inhaler that includes an internal air-operated auditory warning device that generates a pleasant musical tone to alert a user that he/she is inhaling too vigorously or rapidly.

In this regard, the present invention motivates a child to inhale willingly and effectively by the use of one or more breath-driven (i.e. inhalation/exhalation-driven) incentive toys attached to a conventional inhalation apparatus In use, the reward enjoyed by the infant or small child is directly proportional to the efficiency of inhalation and the amount of medication administered to the patient. The modular incentive inhaler device of the present invention also fosters a correct breathing technique in the child, because shallow breathing, such as hyperventilation, is insufficient to adequately activate the incentive toys. By these means, asthmatic, emphysemic and other sick children/infants are effectively treated, and encouraged to overcome their fear and mistrust of inhalers and gas/aerosol/powder delivery devices.

In work leading up to the present invention, the inventors also realised that the mere attachment of toys to a conventional inhaler device, whilst providing an incentive to the juvenile user, did not overcome the further problem of contamination with the medicament contained in inhaled or exhaled air The inventors overcame contamination of the incentive toy(s) with residual medicaments by the provision of removable filters between the incentive toys and those components comprising a conventional inhaler device. Moreover, the inventors also provided a means of minimising contamination of incentive toys with exhaled air by the inclusion of a filter between the mask and the toy containing module.

Accordingly, one aspect of the present invention provides an incentive inhaler device comprising:
 (i) an inhalation device comprising a mask or mouthpiece and a connector that is linkable to a drug delivery device or other device for the delivery of an aerosol, powder or gas; and
 (ii) one or more external visible and/or audible inhalation/exhalation-driven incentive toys, wherein each of said toys is separated from one or more components of said inhalation device (i) by one or more valves, filters or baffles to ensure directional flow of inhaled/exhaled air which drives said toys and/or filters to minimise the contaminating effects of drugs and/or condensation.

Preferably, said valves, filters or baffles that ensure directional air flow and/or filtration are positioned within a conduit that provides for the attachment of said inhalation/exhalation-driven incentive toy(s).

In a preferred embodiment, the present invention provides an incentive inhaler device comprising:
 (i) an inhalation device comprising a conduit that is operably connected at one end to a mask or mouthpiece and at the other end to a connector that is linkable to a drug delivery device or other device for the delivery of an aerosol, powder or gas, wherein said conduit comprises one or more internal valves, filters or baffles to ensure directional flow of inhaled/exhaled air and/or to ensure proper filtration of exhaled or inhaled air; and
 (ii) one or more external visible and/or audible inhalation/exhalation-driven incentive toys, wherein each of said toys is operably connected to said conduit.

Preferably, the modular incentive inhaler device of the present invention further includes a spacer positioned between said inhalation/exhalation mask and said connector. More preferably, the spacer is positioned between said conduit and said connector. In an alternative embodiment, the spacer is positioned between said inhalation/exhalation mask or mouthpiece and said conduit A second aspect of the invention provides an incentive inhaler device comprising: (i) a mask; (ii) a connector that is linkable to a drug delivery device or other device for the delivery of an aerosol, powder or gas; (iii) two inhalation/exhalation-driven incentive toys; and (iv) a conduit, wherein said conduit comprises three adaptor ends that are connected separately to said mask, connector and incentive toys and wherein said conduit comprises a one-way valve in sealable engagement with the interior wall thereof positioned in the adaptor end that is in engagement with said connector the adaptor to ensure directional flow of inhaled air from the linkable drug delivery device, and wherein each of said incentive toys is separated from said connector by said one-way valve. This aspect of the invention also provides for the option of a filter in one of the other adaptor ends of the conduit which minimises the contamination of incentive toys with particles, microbes and/or condensation present in exhaled air A third aspect of the invention provides an incentive inhaler device for administering anaesthetic comprising: (i) a mask; (ii) a drug delivery tube that is linkable to a drug delivery device or other device for the delivery of an aerosol, powder or gas; (iii) one or more exhalation-driven incentive toys; and (iv) a conduit, wherein said conduit comprises three adaptor ends that are connected separately to said mask, drug delivery tube and incentive toys and wherein said conduit comprises a first one-way valve in sealing engagement with the interior wall of the adaptor juxtaposed to the incentive toys to prevent the flow of inhaled air from the incentive toys to the mask. This aspect of the invention also provides for the option of a filter in one of the other adaptor ends of the conduit which minimises the contamination of incentive toys with particles, microbes and/or condensation present in exhaled air.

A fourth aspect of the invention provides a connector that is linkable to a drug delivery device or other device for the delivery of an aerosol, powder or gas for use with an incentive inhaler device comprising:
 (i) an drug delivery receiving means comprising an aperture at one end to sealably-engage the drug delivery device such that minimum leakage and preferably, no leakage of the chemical compound or drug occurs between the connector and the drug delivery device linked thereto; and
 (ii) a threaded portion or snap-lock to releasably- and sealably-engage said connector to the mouthpiece or mask or other component to which said connector is connected or juxtaposed in the assembled incentive inhaler device.

A fifth aspect of the present invention provides a kit comprising two or more of the above connectors, wherein each of said connectors comprises a drug delivery receiving means having an aperture of different dimensions or shape and substantially identical threaded portions or snap-locks such that they are capable of being releasably- and sealably-engaged with the same mouthpiece or mask or other component in the assembled incentive inhaler device.

A sixth aspect of the present invention provides a flexible adaptor end of the connector such that it renders the connector compatible with a variety of drug delivery devices.

A seventh aspect of the present invention provides a method of administering a inhalable medicament to an infant or child subject comprising activating, during the inhalation and/or exhalation phase of breathing of said subject, one or more external visible and/or audible inhalation/exhalation-driven incentive toys that are operably connected to an incentive inhalation device described herein according to any one or more of the embodiments described herein.

The above and other novel features of the present invention will be apparent from the following detailed description, and the accompanying examples and drawings.

DETAILED DESCRIPTION OF THE PREFERRED EMBODIMENTS

Figure 1:
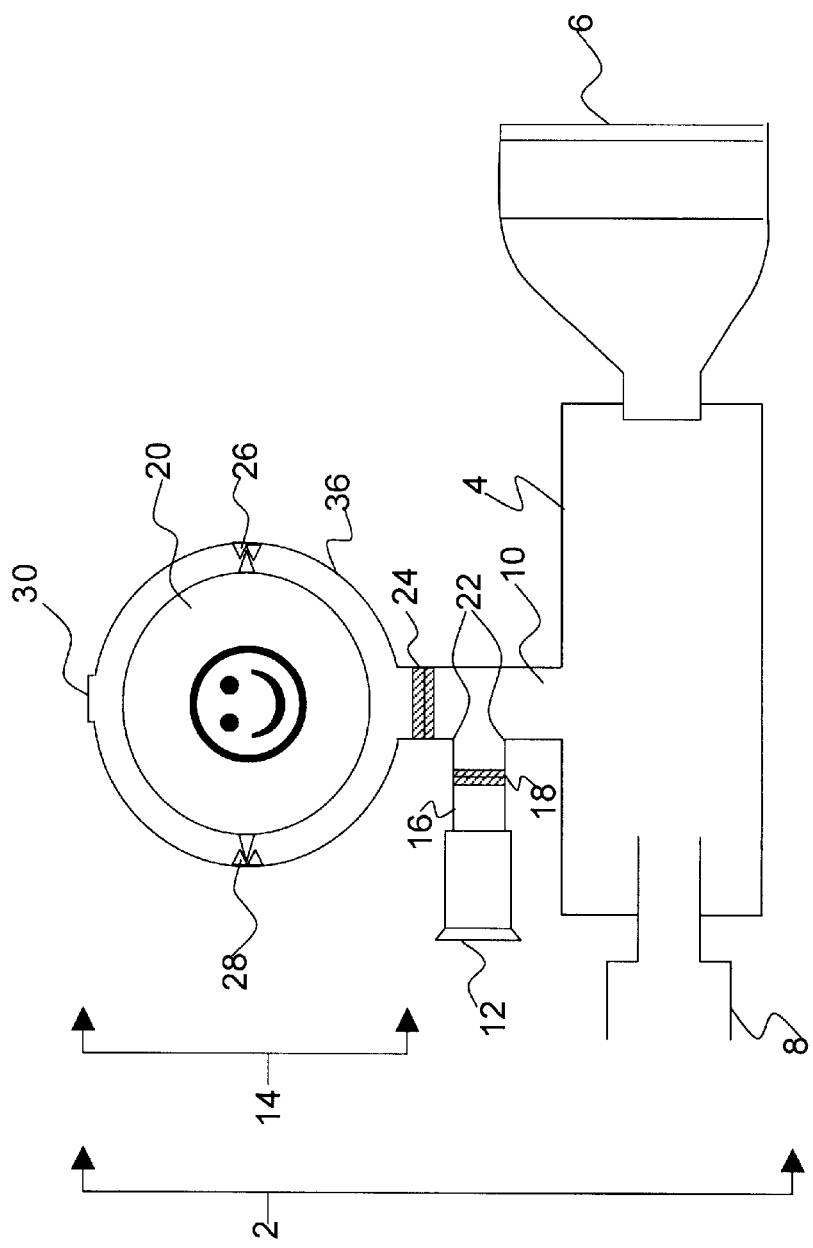
FIG. 1 is a sectional view of one embodiment of the modular incentive inhaler device, wherein an inhalation-driven and an exhalation-driven incentive toy are positioned between the mask (6) and the linkable drug delivery device via a conduit.

One aspect of the present invention provides an incentive inhaler device comprising:
(i) an inhalation device comprising a mask or mouthpiece and a connector that is linkable to a drug delivery device or other device for the delivery of an aerosol, powder or gas; and
(ii) one or more external visible and/or audible inhalation/exhalation-driven incentive toys, wherein each of said toys is separated from one or more components of said inhalation device (i) by one or more valves, filters or baffles to ensure directional flow of inhaled/exhaled air which drives said toys and/or to ensure filtration of exhaled air.

Preferably, said valves, filters or baffles that ensure directional air flow air are positioned within a conduit that provides for the attachment of said inhalation/exhalation-driven incentive toy(s).

More preferably, the valve employed in the present invention is a one-way valve. The one-way valves used in the present invention are preferably butterfly valves or, in the case of those devices wherein the valve further provides for venting of exhaled air/medicament mixtures (see Examples 2 and 4 described herein), a flap-type valve can be used, such as that described in U.S. Pat. No. 4,470,412 and/or Australian Patent No. 620375.

As used herein, the terms "inhaler device", "inhalation device" or similar term shall be taken to refer to a device or apparatus that is suitable for use as an inhaler to administer a chemical compound or drug, or a medicament, pharmaceutical composition, adjuvant, vaccine, antifungal composition, antibacterial composition, antiviral composition or other composition of matter comprising said chemical compound or drug including anaesthetics, in the form of a gas, powder or aerosol to the respiratory system of a human or animal subject by oral inhalation.

The term "incentive inhaler device" refers to an inhaler device as defined herein that encourages a user or a group of users to employ said inhaler device in the self-delivery of one or more compounds or drugs or compositions of matter comprising same. The term "incentive inhaler device" extends further to those inhaler devices that both encourage a user or group of users and provide for improved efficiency of self-delivery of the compounds or drugs or compositions of matter comprising same. By "self-delivery" is meant that the user or group of users administers said compounds or drugs or compositions of matter to their own respiratory system by voluntary inhalation thereof.

The present invention is not to be limited by the material used to construct any one or more of the components thereof and persons skilled in the art will be aware of a range of materials suitable for use in constructing the subject incentive inhaler device, including rubber, metals, synthetic polymers, in particular a plastic such as polycarbonate, polyvinyl chloride, polyvinyl acetate or elastomer, amongst others.

Additionally, for those applications wherein the user is a child or infant, the unit is optionally designed to avoid sharp edges that may injure the child or infant in use.

The mask or mouthpiece is preferably comprised of rubber and/or plastic material and may be any functional shape or configuration known to those skilled in the art, including a tube, nasal tube, catheter, or mask, that is capable of providing delivery of a gas, powder or aerosol to the respiratory system of a human or animal subject.

Preferably, the incentive inhaler device of the present invention at least comprises a mask. Advantageously, the mask is moulded from rubber or plastic, preferably flexible plastic or rubber, and adapted to conform to the face of the user, for example the face of a human infant or small child, such that said mask fits over the nose and mouth of said user and is in sealing contact with said face. As exemplified herein, it is particularly preferred that the mask comprises a substantially frustoconical portion that is flanged at the open base to receive a flexible rubber or plastic gasket that in use is secured in pneumatically-sealed relation to the face of the user. Preferably, the mask is transparent or translucent to minimise potential fear associated with having an opaque object brought to a child's face.

The connector may comprise a plate or a hollowed cylindrical or other-shaped metal or plastic unit that includes a drug delivery device receiving means comprising an aperture at one end to sealably-engage the drug delivery device, such that minimum leakage and preferably, no leakage of the chemical compound or drug occurs between the connector and the drug delivery device linked thereto. Accordingly, the aperture of the drug delivery device receiving means is designed to precisely receive the dispensing end of the drug delivery device.

The term "sealably-engage" or similar term shall be taken to mean that two components are engaged, connected or juxtaposed in the assembled or partially-assembled incentive inhaler device of the present invention in a manner to prevent the escape of the drug or medicament at a level sufficient to prevent inhalation/exhalation-driven activation of one or more incentive toys of said device or to impair drug delivery to the patient.

As used herein, the "dispensing end" of the drug delivery device refers to the portal or end of the drug delivery device from which the drug or medicament is ejected into the incentive inhaler device or, in the absence of the inventive device, the portal or end from which the drug or medicament is ejected from the drug delivery device into the environment of the patient's respiratory system.

As will be known to those skilled in the art, the shape of the dispensing end of a drug delivery device may vary considerably. Advantageously, the present invention provides for the insertion of a range of different connectors suitable for use with drug delivery devices having differently-shaped dispensing ends. According to this embodiment, releasable engagement of the drug delivery device to the drug delivery device receiving means permits re-use of the incentive inhaler device, by virtue of having drug delivery device receiving means that vary in shape and size and, as a consequence, accommodate different-shaped and/or different-sized drug delivery device dispensing ends.

Methods for releasably-engaging such components together are known in the art and include, for example, screwing, clipping, sliding, etc.

Alternatively, the receiving means may also be constructed in such a manner that enables it to transform in size and shape to fit a number of drug delivery devices. For example, the drug delivery device receiving means may be formed from a stretchable or flexible material which can distort to cover the drug delivery device dispensing end.

Alternatively, the receiving means may also be adapted to receive a plurality of drug delivery device dispensing ends. For example, a single connector may possess a plurality of different shaped or sized drug delivery device receiving means. Such a connector may be used to deliver more than one medicament to the inhaler device of the present invention.

Preferably, the connector according to this embodiment comprises:
(i) an aperture at one end to sealably-engage the drug delivery device such that minimal leakage of the chemical compound or drug occurs between the connector and the drug delivery device linked thereto; and
(ii) a threaded portion or snap-lock to releasably- and sealably-engage said connector to the mouthpiece or mask or other component to which said connector is connected or juxtaposed in the assembled incentive inhaler device of the present invention as described herein.

Preferably, the connector comprises a male or female threaded portion that screws into an opposing female or male threaded portion, respectively, in the component to which said connector is juxtaposed in the assembled incentive inhaler device of the present invention.

The drug delivery device may be any device known to those skilled in the art for dispensing a medicament or chemical or a composition comprising same in gas, aerosol or powder form, including but not limited to an anti-inflammatory compound, a synthetic or natural steroid (eg a corticosteroid), a bronchodilator, a vasodilator, a homoeopathic medicine, an antihistamine, an antibiotic, a cough mixture, a tranquilliser, an anaesthetic, or an adrenergic receptor agonist or antagonist such as a beta-agonist or beta-blocker, a therapeutic gas such as oxygen, nitrogen dioxide, nitrous oxide or a gaseous mixture such as air or Entonox, amongst others, or a combination of one or more of said drugs. The present invention is not to be limited by the nature of the compound dispensed from the drug delivery device, the only requirement being that said drug is administrable to a patient in need of treatment by means of inhalation.

Preferably, the drug delivery device is a Metered-dose inhaler (MDI). Hand-held MDI devices are a preferred form of treatment for common respiratory ailments, because the delivery of medication directly to its intended site of action in the respiratory system of the patient allows a reduction in the dosage administered.

Optionally, the present invention may also include a means for enclosing the drug delivery device. For example, where the drug delivery device is an asthma pump, the present invention optionally includes a sealing means that covers at least part of said drug delivery device. Alternatively, as exemplified in FIG. 6 incorporated herein, a rubber sleeve may cover the drug delivery device, which sleeve may incorporate designs/colours and/or toys that are capable of distorting upon inhalation and/or exhalation, to reduce leakage of a medicament via the MDI cylinder housing and/or to improve the function of inhalation/driven incentive toys.

The incentive toy of the incentive inhaler device of the present invention may be any toy that is capable of being activated by inhalation and/or exhalation, the only requirements being that said toy provides a sufficient stimulus to a child or infant user to motivate said user to inhale willingly and effectively through the incentive inhaler device, particularly when said device is in operable engagement with a drug delivery device.

As used herein, a "toy" is any device capable of giving amusement to a user thereof and, in particular, a device that produces an audible and/or a visual signal, such as a siren, flashing light or colour, or movement, amongst others.

In the context of the present invention, the term "incentive toy" refers to a toy as defined herein that, by virtue of the quality of the audible and/or a visual signal produced therefrom, is capable of inducing a child or infant user to repeated use thereof.

Any type of inhalation and/or exhalation-driven incentive toy(s) may be used in the present invention For example, the toy may be a whistle or it may be contained in a modular or injection moulded unit which permits fluid activation. Such a unit might, for example, contain an air driven device including (but not limited to) pneumatic tops, wheels, jack-in-the-boxes, propellers, bubble-blowers, rotating figures, spinning discs, kaleidoscopes and toys incorporating objects floating on or driven by air.

In a particularly preferred embodiment of the present invention, the incentive toy is a coloured spinning disc, such as a spinning disc containing a colourful representation of a clown.

Alternatively or in addition, the particularly preferred embodiment of the present invention employs a whistle, more preferably a detachable whistle that permits the two-way passage of air however is activated unidirectionally, such that activation of the whistle by either inhalation or exhalation is effected by reversing the direction of attachment of said whistle to the incentive inhaler device. Whistles conforming to this specification are well-known in the art, such as the Sirenen™ produced by Heuler (Germany). Alternatively or in addition, bi-directional whistles which are activated both on inhalation and exhalation may be used.

Inhalation and/or exhalation-driven incentive toy(s) may be located anywhere in the incentive inhaler device of the present invention, the only requirements being that they are operationally separated therefrom by one or more one-way valves and/or filters and activated by exhalation or inhalation. The purpose of this arrangement is to ensure directional flow of air and medicament through or around the incentive toy during the exhalation or inhalation phase of breathing, as appropriate, and/or to ensure that any exhaled air/medicament mixture is kept away from the incentive toys to reduce contamination therewith. For example, the incentive toys may be placed in operable association with the mask or mouthpiece and/or the connector and/or the drug delivery device receiving means. The incentive toy(s) may also be placed in operable association with a spacer member if it is included in the arrangement.

When an inhalation-driven incentive toy is connected to the incentive inhaler device of the present invention, air containing the medicament is drawn through or past the inhalation-driven incentive toy thereby activating it whereupon it may be inhaled with medicament.

The device of the present invention according to the above embodiments can also include a valve between the conduit and the connector (which adjoins via an optional spacer to the drug delivery means), to ensure that exhaled air is not blown back through the connector and/or toy modules.

Alternatively or in addition, a replaceable filter can be placed in the conduit, between the mask and the incentive toys, to minimise the contamination from microbes, condensation and/or particles in exhaled air.

In an alternative embodiment, air containing the medicament may be inhaled through a parallel arrangement of conduits which are operationally connected to the incentive inhalation device to ensure drug delivery as said incentive inhalation device is activated. In such an example, the inhaled air travels past the inhalation-driven incentive toy however does not mix with or come in contact with the air containing the medicament until it enters the patient's airways. This embodiment of the present invention is also compatible with the provision of valves and/or filters to ensure that the exhaled air is not blown back through the connector/spacer module and/or that the device become contaminated.

In a further alternative embodiment of the present invention, inhalation-driven incentive toys can be electrically-activated, such that the level of activation of the toy is proportionally linked to the amount of air containing the medicament that is inhaled by the patient.

Wherein an exhalation-driven incentive toy is employed, exhaled air is preferably channelled through or past the exhalation-driven incentive toy thereby activating it before being vented from the device It will be appreciated that some embodiments described above for activation of an inhalation-driven toy may likewise be employed with an exhalation-driven toy.

When the toy is driven by both the inhalation and exhalation of air, air is preferably drawn into the device through or past an inhalation-driven incentive toy and enters the inhalation device in conjunction with medicament dispensed from the drug delivery device that is in engagement with the incentive inhalation device of the present invention. Upon exhalation, fluid in the form of expired air is exhaled through or past the exhalation-driven incentive toy before being vented from the device.

In one embodiment of the present invention, the incentive inhaler device includes a single inhalation-driven incentive toy. According to this embodiment, said incentive inhaler device can include one or more means to exhale air through the mask or mouthpiece or alternatively, it may need to be removed from the patient's face prior to exhaling.

Preferably, exhaled air containing medicament can be exhaled through the device by either blowing it into the mask or mouthpiece, where it is subsequently vented from the incentive inhaler device via the drug delivery device (depending on the type of drug delivery device used), or via the incentive toy unit or, if the drug delivery device is a sealed unit through which exhaled fluid may not pass, the exhaled air containing medicament may be vented from said device via one or more apertures formed therein. Accordingly, the present invention clearly contemplates an incentive inhaler device having separate exhaust tubes for venting exhaled air containing the medicament.

In a particularly preferred embodiment of the present invention, the exhaled air containing the medicament is exhaled through the device by either blowing it into the mask or mouthpiece, where it is subsequently vented from the incentive inhaler device via the incentive toy unit, wherein said toy unit is also activated by the exhaled air. In such cases, a filter can be placed between the mask and the incentive toy module to minimise contamination.

In a further alternative embodiment of the present invention, the incentive inhaler device can include a single exhalation-driven incentive toy. Where the spacer device only includes such a toy, a means through which fluid can be inhaled may or may not be provided. Desirably the device contains a means for inhalation. This may be achieved, for example, through the exhalation-driven incentive toy unit or through an alternative route provided in the spacer device. For example, fluid in the form of air may be drawn through the drug delivery service (depending on the type of drug delivery device used) into the spacer member or if delivery device is sealed, fluid may be drawn through one or more apertures provided in the spacer member. In another embodiment the device may contain separate inhalation conduits.

In use, medicament is released into the incentive inhaler device via the connector and is contained therein and/or is released into the mask or mouthpiece. In the case of medicaments comprising powders, those skilled in the art will be aware that is possible for such medicaments to be released directly into the mask or mouthpiece for inhalation by the patient. The patient inhales the medicament by drawing air containing said medicament through the mask or mouthpiece via the connector or an inhalation aperture. Upon exhaling, the patient blows expired air into the incentive inhaler device which directly or indirectly leads to the activation of the exhalation-driven incentive toy therein causing activity in said toy (eg. in the form of a sound in the case of a whistle or in the form of movement in most other pneumatic activated toys). In such cases, a filter can be placed between the mask and the incentive toy module, to minimise contamination.

The present invention is not be limited to the use of a single inhalation- and/or exhalation-driven incentive toy and the present invention clearly contemplates a plurality of inhalation- and/or exhalation-driven incentive toys in association with the incentive inhaler device, as exemplified herein. Wherein the incentive inhaler device does contain a plurality of different inhalation- and/or exhalation-driven incentive toys, these may be arranged such as to be activated simultaneously upon inhalation and/or exhalation or alternatively, they may act independently of each other such that one or more toys is activated by inhalation and the other toy(s) is (are) activated by exhalation.

Preferably, wherein multiple incentive toys are employed, said toys are arranged in such a manner as to indicate the breathing pattern of the patient using the incentive inhaler device. For example, the inhalation and/or exhalation-driven incentive toys may be whistles, one of which activates when medicament is being inhaled and then another upon exhalation. Alternatively, a different toy unit may be employed during the inhalation phase of breathing to that which is employed during the exhalation phase. In the particularly preferred embodiment of the present invention, the incentive toys comprise both whistles and spinning discs arranged such that the whistle is activated by either inhalation or exhalation, depending upon its orientation and the spinning disc is activated by exhalation. Accordingly, this embodiment of the present invention provides for both toys to be activated by inhalation or alternatively, for the whistle to be activated by the inhalation and the spinning disc to be activated by exhalation.

Preferably the spacer device has both an inhalation-driven incentive toy and an exhalation-driven incentive toy connected to the spacer member via a single conduit through which inhaled and exhaled gases may flow.

The directional control of airflow through the incentive inhaler device is achieved by using a one-way valve. Wherein the one-way valve is used in conjunction with an inhalation-driven incentive toy, it is preferred that said one-way valve allows entry of inhaled air containing the medicament from the drug delivery means and past or through the incentive toy, whilst retarding the free flow of air in the other direction (i.e. back into the drug delivery means). Wherein the one-way valve is used in conjunction with an exhalation-driven incentive toy, it is preferred that said one-way valve allows the venting of exhaled air containing the medicament from the incentive drug delivery means past or through the incentive toy unit, whilst retarding the free flow of air in the other direction. Preferably, more than a single one-way valve is employed. Preferably one or more baffles or filters is also included between the mask and the incentive toy module, to minimise contamination.

The one way valve(s) is(are) preferably contained within a conduit located between the mask or mouthpiece and the connector. Accordingly a further aspect of the present invention provides an incentive inhaler device comprising:

(i) an inhalation device comprising a conduit that is operably connected at one end to a mask or mouthpiece and at the other end to a connector that is linkable to a drug delivery device or other device for the delivery of an aerosol, powder or gas, wherein said conduit comprises one or more internal valves, filters or baffles to ensure directional flow of inhaled/exhaled air and/or filtration of exhaled air; and (ii) one or more external visible and/or audible inhalation/exhalation-driven incentive toys, wherein each of said toys is operably connected to said conduit.

The conduit must be in sealable engagement with both the mouthpiece and the connector, to prevent the leakage of air from the incentive inhaler device Preferably, the conduit is made of rigid plastic or rubber material and of cylindrical or conical shape.

In a particularly preferred embodiment, the conduit comprises at least three adaptor ends for connection of the mask or mouthpiece, the connector and one or more incentive toy units. According to this embodiment, the one-way valve is positioned within said conduit in sealable engagement with the interior wall thereof at or within any one or more of said adaptor ends. For example, a one-way valve can be placed within said conduit in sealable engagement therewith and at or within the adaptor end that connects to the connector, such that medicament or air/medicament mixture can be drawn into the mask or mouthpiece from the drug delivery means but not in the opposite direction. Alternatively or in addition, the one-way valve can be placed within said conduit in sealable engagement therewith and at or within the adaptor end that connects to the mask or mouthpiece, such that medicament or air/medicament mixture can be drawn into the mask or mouthpiece from the conduit but not in the opposite direction, in which case the exhalation phase must accompany removal of the mask or mouthpiece from the patient's face or airway. Alternatively or in addition, the one-way valve can be placed within said conduit in sealable engagement therewith and at or within the adaptor end that connects to the incentive toy unit, such that, in the case of an inhalation-driven incentive toy unit, air can be drawn over said incentive toy unit and into the mask or mouthpiece via the conduit but not in the opposite direction and, in the case of an exhalation-driven incentive toy unit, exhaled air can pass through or over said toy unit from the mask or mouthpiece but not in the opposite direction.

Wherein the one-way valve is positioned within the conduit in the adaptor end that is in engagement with the incentive toy, said valve can further serve to prevent the patient from re-breathing the exhausted air/medicament mixture. Without limiting the present invention, this embodiment is particularly useful in applications of the present invention to the delivery of anaesthetics.

The present invention clearly provides for the attachment of one or more incentive toy units to the same or different adaptor ends of the conduit. Preferably, wherein multiple toy units are in operable engagement with the same adaptor end of the conduit, these are in linear engagement with each other. In a particularly preferred embodiment of the present invention, two incentive toys are linked in linear engagement with each other such that one toy unit is activated by inhalation and one or both toy units are activated by exhalation.

The present invention also provides for the attachment of a filter between the mask and the incentive toy module, to minimise contamination.

As will be apparent to those skilled in the art, wherein the toy unit is activated by both inhalation and exhalation or alternatively, wherein multiple toy units are linked via the same conduit adaptor end in linear engagement such that they are collectively or individually activated by both breathing phases, it is inappropriate to include a one-way valve at or within the adaptor end of the conduit that connects to the incentive toy unit.

In a particularly preferred embodiment of the present invention, there is provided an incentive inhaler device comprising:

(i) a mask;

(ii) a connector that is linkable to a drug delivery device or other device for the delivery of an aerosol, powder or gas;

(iii) two inhalation/exhalation-driven incentive toys comprising an inhalation/exhalation-driven whistle and an exhalation-driven spinning disc; and (iv) a conduit, wherein said conduit comprises three adaptor ends that are connected separately to said mask, connector and incentive toys and wherein said conduit comprises a one-way valve in sealable engagement with the interior wall thereof positioned in the adaptor end that is in engagement with said connector the adaptor to ensure directional flow of inhaled air from the linkable drug delivery device, wherein each of said incentive toys is separated from said connector by said one-way valve.

Preferably, the conduit further comprises one or more venturi units in sealable engagement with the interior wall thereof and at or within any one or more of said adaptor ends, so as to facilitate the flow of air and/or air/medicament mixture in the same direction as any one-way valve that is positioned within the same adaptor end. Alternatively, if no one-way valve is present within the same adaptor end, the venturi unit is generally positioned to provide for increased air velocity into or from the mask or mouthpiece or over one or more of the incentive toy units.

Those skilled in the art will be aware that a "venturi" is a hollow device through which air can pass bi-directionally, which device generally comprises a frustoconical portion tapered so as to increase the velocity of local air flow there through in the same direction as the taper.

In a particularly preferred embodiment of the present invention, a venturi is positioned in sealable engagement with the interior wall of the conduit adaptor end connecting the incentive toy(s) such as to facilitate the flow of exhaled air over said incentive toy(s). According to this embodiment, the venturi is preferably positioned in front of the incentive toy with the tapered end of the venturi device directed thereon.

Alternatively, in the case of inhalation-driven incentive toys, the venturi can be placed within the incoming air portal and in sealable engagement with the interior wall of said portal, and preferably positioned in front of the incentive toy with the tapered end of the venturi device directed thereon.

In a particularly preferred embodiment of the present invention, there is provided an incentive inhaler device comprising:

(i) a mask;

(ii) a connector that is linkable to a drug delivery device or other device for the delivery of an aerosol, powder or gas;

(iii) two inhalation/exhalation-driven incentive toys comprising an inhalation/exhalation-driven whistle and an exhalation-driven spinning disc; and (iv) a conduit, wherein said conduit comprises three adaptor ends that are connected separately to said mask, connector and incentive toys and wherein said conduit comprises:

(a) a one-way valve in sealable engagement with the interior wall thereof positioned in the adaptor end that is in engagement with said connector the adaptor to ensure directional flow of inhaled air from the linkable drug delivery device; and (b) a venturi in sealable engagement with the interior wall thereof positioned in the adaptor end that is in engagement with said incentive toys and positioned so as to increase the velocity of exhaled air/medicament over said incentive toys, wherein each of said incentive toys is separated from said connector by said one-way valve.

In a preferred embodiment, the incentive inhaler device of the present invention further includes a spacer positioned between the mask or mouthpiece and the connector.

Those skilled in the art will be aware that the word "spacer" refers to a chamber into which a medicament or drug or other composition may be released, such as by ejection from an MDI, wherein said spacer retains the medicament or drug or other composition until the patient is ready to breathe inhale it. Spacer devices allow for the deceleration of gas-borne particles that can be expelled from some MDI devices at high velocity. In the absence of a spacer device, the excessive velocity of the spray allows the particles to coat the throat of the patient and mouth, causing wastage of drug and undesirable side effects Additionally, spacers do not require such precise coordination of inspiration with the actuation of the drug delivery device or MDI, since they can store the drug dose for inhalation in subsequent breaths.

Spacers are provided in various shapes and sizes and the present invention is not to be limited by the shape or size of the spacer unit, or the material used to construct the spacer unit. An exemplary spacer unit is described in Australian Patent No. 623991.

The spacer unit can include, at one end, an adaptor for sealably-receiving the connector comprising the drug delivery device receiving means. Preferably, the adaptor will comprise a threaded portion or snap-lock to releasably- and sealably-engage said connector to the spacer. More preferably, the spacer adaptor comprises a male or female threaded portion that screws into an opposing female or male threaded portion respectively, in the connector. In use, the connector comprising the drug delivery device receiving means may be interchanged, depending upon the size and shape of the dispensing end of the drug delivery means, to ensure that an airtight engagement is formed between the drug delivery device, the connector and the spacer.

Alternatively, the spacer and connector may be constructed as an integral unit, preferably, moulded from metal, plastic or rubber material, such as by plastic injection moulding. According to this embodiment, it is necessary for the spacer/connector combination to be changed depending upon the size and shape of the dispensing end of the drug delivery means that is used to deliver the medicament or drug to the spacer.

The spacer unit can also include at least a means to directionally control airflow away from the drug delivery device receiving means on the connector in the assembled device. Preferably a one-way valve is used which is capable of at least retarding passage of air back into the drug delivery device while allowing the free flow of air out of the device. Such a valve is preferably positioned within, or is operationally connected to the spacer in a manner which allow a patient to unidirectionally draw a drug from the spacer.

In a preferred embodiment of the present invention, the incentive inhaler device is a modular incentive inhaler device. By "modular incentive inhaler device" is meant an incentive inhaler device as defined herein that is composed of separable components that may be changed in their configuration, such as by directional reversal of one component relative to another component, or the spatial rearrangement of one or more components with respect to each other, or the inclusion or omission of any optional or preferred component, integer or feature.

Accordingly, each of the components of said incentive inhaler device are connectable via an appropriate adaptor, such as an adaptor having a threaded portion or snap-lock to releasably- and sealably-engage said connector to the conduit, amongst others. In a particularly preferred embodiment, the mask or mouthpiece, the spacer, the conduit, the connector and the incentive toys comprising the incentive inhaler device are connected or engaged via a snap lock mechanism comprising a first adaptor that inserts co-axially into a second adaptor.

The present invention clearly contemplates the construction of any two or more components of the incentive inhaler device as an integral unit, such as from moulded plastic material.

In one embodiment, the spacer is positioned between the inhalation/exhalation mask or mouthpiece and the conduit, in which case the conduit must be in sealable engagement with the connector. As will be apparent to those skilled in the art, this embodiment of the present invention requires both inhaled and exhaled air to pass through the spacer.

As with other embodiments of the present invention, the means for sealably-engaging the conduit and the connector may comprise an adaptor having a threaded portion or snap-lock to releasably- and sealably-engage said connector to the conduit. More preferably, such means will comprise a snap-lock between one adaptor end of the conduit and the connector. Alternatively, the conduit and connector may be constructed as an integral unit, preferably, moulded from metal, plastic or rubber material.

Similarly, the spacer can be connected to both the inhalation/exhalation mask or mouthpiece and the conduit by means of an adaptor or the spacer/mask or mouthpiece/conduit combination or a part thereof can be manufactured as an integral unit.

Preferably, the spacer is positioned between the conduit and the connector. Wherein incentive toys are connected to the conduit, this arrangement avoids the need to draw the inhaled air/medicament mixture past or through the toy before it reaches the lungs, thereby minimising contamination of toys with the medicament.

As will be apparent from the preceding disclosure, the spacer can be connected to both the conduit and the connector by means of an adaptor or the conduit/spacer/connector combination or a part thereof can be manufactured as an integral unit.

Wherein the incentive toy(s) are not in engagement or gaseous communication with the spacer unit, the incentive inhaler device may have a valve which limits or prevents the entry of exhaled air/medicament mixture into the spacer. In such an embodiment of the present invention, an incentive toy unit may be positioned between the valve and the mask or mouthpiece.

Alternatively, such an external incentive toy module may be attached to a valveless spacer without an intervening valve, allowing some recycling of drugs still present in exhaled air back into the spacer.

However, the present inventors have found that, wherein the incentive toy linked to a spacer that is positioned between the connector and the conduit is an inhalation-driven incentive toy, it is particularly preferred for the drug delivery device to be sealed for the toys to be activated by inhalation. Such sealing of the drug delivery device may take the form of a cap placed over said device.

Preferably, a one-way valve is located between the drug delivery device receiving means on the connector and the inhalation and/or exhalation-driven incentive toy.

In a preferred embodiment of the present invention, there is provided an incentive inhaler device comprising:

(i) a mask;
(ii) a connector that is linkable to a drug delivery device or other device for the delivery of an aerosol, powder or gas;
(iii) two inhalation/exhalation-driven incentive toys comprising an inhalation/exhalation-driven whistle and an exhalation-driven spinning disc; and
(iv) a spacer in engagement at one end with said connector and at the other end with a conduit, wherein said conduit comprises three adaptor ends that are connected separately to said mask, spacer and incentive toys and wherein said conduit comprises a one-way valve in sealable engagement with the interior wall thereof positioned in the adaptor end that is in engagement with said spacer to ensure directional flow of inhaled air from the linkable drug delivery device, wherein each of said incentive toys is separated from said connector by said one-way valve.

In a particularly preferred embodiment, the incentive inhaler device comprises:

(i) a mask;
(ii) two inhalation/exhalation-driven incentive toys comprising an inhalation/exhalation-driven whistle and an exhalation-driven spinning disc; and
(iii) an integral spacer/connector that is linkable at one end to a drug delivery device or other device for the delivery of an aerosol, powder or gas, wherein said spacer/connector is in engagement at the other end with a conduit having three adaptor ends that are connected separately to said mask, spacer/connector and incentive toys and wherein said conduit comprises:
(a) a one-way valve in sealable engagement with the interior wall thereof positioned in the adaptor end that is in engagement with said spacer/connector to ensure directional flow of inhaled air from the linkable drug delivery device; and
(b) a venturi in sealable engagement with the interior wall thereof positioned in the adaptor end that is in engagement with said incentive toys and positioned so as to increase the velocity of exhaled air/medicament over said incentive toys, wherein each of said incentive toys is separated from said spacer/connector by said one-way valve.

The provision of an optional anti-contamination filter in the conduit between the mask and the incentive toy module is also contemplated by the present invention.

The incentive inhaler device of the present invention may also include one or more venting means to allow for the escape of exhaled air. According to this embodiment, the means to directionally control airflow should preferably be located between the drug delivery device receiving means and the venting means.

Optionally, in those applications of the present invention to the administration of anaesthetics, it is preferred for the venting means to include a scavenger pipe or tube to channel the exhaled anaesthetic/air mixture away from the atmosphere of the surgery or operating theatre, thereby avoiding any person nearby from breathing the exhaled anaesthetic gases. Advantageously, such a scavenger system can be placed in engagement with the exhalation-driven incentive toy unit, such that exhaled air passing through or over the unit is then collected into the scavenger system.

Optionally, the incentive inhaler device of the present invention can also include an anti-microbial, anti-condensation and/or anti-particle filter, preferably placed between the mask or mouthpiece and the conduit or spacer or connector, as the case may be. The provision of such a filter is particular desirable wherein the incentive inhaler device is used to administer a pre-operative anaesthetic compound and/or to reduce the inhalation of allergenic particles by the patient.

Optionally, the incentive inhaler device of the present invention may also include one or more turbine-driven incentive toys. As used herein the term "turbine-driven incentive toy" refers to an incentive toy that is driven by inhalation and/or exhalation via a rotor A turbine rotor is generally activated by a bi-directional flow of air and, as a consequence, in the absence of a one-way valve system, the turbine-driven incentive toy will be activated by both inhalation and exhalation. According to this embodiment of the present invention, the rotor housing can be located in the mask, conduit, spacer or in physical relation to other incentive toys present therein. Whilst there is no requirement for a turbine-driven incentive toy to be separated from one or more components of the incentive inhaler device by one or more valves to ensure directional flow of inhaled/exhaled air which drives said toys, however such an arrangement is clearly possible.

A further aspect of the present invention provides a method of administering a inhalable medicament to an infant or child subject comprising activating, during the inhalation and/or exhalation phase of breathing of said subject, one or more external 20 visible and/or audible inhalation/exhalation-driven incentive toys that are operably connected to an incentive inhalation device described herein according to any one or more of the foregoing embodiments.

By "administering" is meant the stimulation or encouragement of self-delivery of a medicinal, anaesthetic, drug, gas, pharmaceutical or other chemical compound or composition comprising same during a therapeutic or prophylactic medical procedure, irrespective of the location at which such procedure is performed (e.g.: in the home or in a doctor's surgery or hospital).

Preferably, in anaesthetic applications as applied to infants and small children, it will be apparent to those skilled in the art that part or all of the incentive inhaler device of the present invention can be dispensed with and replaced by a conventional anaesthetic inhaler once the child has been initially anaesthetised. As will be apparent from the preceding description, the activation of the incentive toys is achieved by inhalation and/or exhalation by the patient. Such activation may comprise the production of any audible and/or visual signal or stimulus, such as such as a siren, flashing light or colour, or movement, amongst others.

Further features of the present invention are more fully described in the following Examples. It is to be understood, however, that this detailed description is included solely for the purposes of exemplifying the invention, and does not in any way limit the present invention.

EXAMPLE 1

An Incentive Inhaler Device Comprising an Inhalation-driven Incentive Toy and an Exhalation-driven Incentive Toy FIG.1 illustrates an incentive inhaler device (2) including a cylindrical or conical shaped connector (4) and a respiration device in the form of a mask (6). Releasably-engaged to the other end of the incentive inhaler device (2) is a drug delivery device receiving means (8) which is adapted to accommodate a drug delivery device (not shown), or alternatively a nebuliser or any other device suitable for delivering inhaled medicament via the receiving means.

Releasably-engaged to the outer surface of the connector (4), and positioned between the drug delivery device receiving means (8) and the mask (6), is a separator element (10). The separator element (10) comprises a conduit that forms the connecting passageway between the inhalation-driven incentive toy unit (12), the exhalation-driven incentive toy unit (14) and the connector.

In use, a drug delivery device is engaged to the incentive inhaler device (2) via the drug delivery device receiving means (8). A metered dose of medicament is released into the connector (4). The mask (6) is brought into sealable contact with a patient's face and then the patient inhales the air mixed with medicament. Upon inhaling, air is drawn into the incentive inhaler device (2) via the inhalation-driven incentive toy unit, which is illustrated as a whistle (12). A siren is sounded as air is drawn through the whistle. Inhaled air passes through the inhalation conduit (16) of the whistle in which there is located a one-way valve (18) and enters the separator (10). The one-way valve prevents the reverse flow of fluid into the inhalation-driven incentive toy unit (12) upon exhalation by the patient. Desirably the valve (18) is activated by negative pressure in the separator element (10), but seals when there is positive pressure in the separator element (10). In a particularly preferred form of the invention, the one-way valve may be adapted to be removed from the inhalation conduit therein facilitating service or replacement of the valve should it cease working in a proper and efficient manner.

As air enters the separator element (10) from the whistle unit (12), it is drawn into the connector (4) and mixes with the medication that has been released into the connector (4). The patient can then inhale the medication via the mask (6).

During the inhalation phase, medicament is prevented from entering the exhalation-driven incentive toy unit (14) by a second one-way valve (24) located between the junction (22) of the inhalation conduit (16) and the separator element (10), which valve (24) opens only when there is a positive pressure in the separator element (10) and seals closed when negative pressure is applied to said separator element (10).

Upon exhalation, fluid is blown back into the connector (4) where it mixes with residual medicament that has not been inhaled. This creates a positive pressure in the connector (4), thereby forcing air/medicament mixture to enter the separator element (10).

As air/medicament mixture moves up the separator element (10), it is prevented from entering the inhalation conduit (16) of the separator element (10) by the one-way valve (18) located therein. Air/medicament mixture passes through the second one-way valve (24) and into the exhalation-driven incentive toy unit (14), thereby activating said toy. The exhalation driven incentive toy unit (14) consists of a transparent sphere (36) in which there is mounted a toy in the form of a colored spinning disc (20) having an image drawn thereon. As exhaled air/medicament mixture is blown into the exhalation-driven incentive toy unit (14), it is forced over the disc (20) causing it to spin on mounts (26) and (28). The air/medicament mixture then passes out of the unit via an air release aperture (30).

The air release aperture (30) is illustrated as a single hole in the top of the exhalation-driven toy unit (14). There may, however, be a plurality of different apertures in the module.

Notwithstanding that the exemplification of the present invention set forth in FIG. 1 illustrates a spinning disc as the exhalation-driven incentive toy and a whistle as the inhalation-driven toy, it should be appreciated that these toy units can be interchanged so as to provide for inhaled air to pass over the spinning disc and exhaled to pass through the whistle. In such a variation of the present exemplified embodiment, valves (24) and (18) are interchanged to achieve the correct passage of air or air/medicament mixture.

Preferably, each incentive toy unit is associated with a particular one-way valve and the valve/toy combination is formed as an integral module. In this instance, the separator element (10) can be adapted to receive either valve/toy module, thereby facilitating the formation of a variety of different configurations of the incentive inhaler device with different inhalation and/or exhalation-driven incentive toys.

Those skilled in the art will recognize that the connector (4) depicted in FIG. 1 may be integral with a spacer unit as hereinbefore defined, or functions as a spacer unit as hereinbefore defined.

EXAMPLE 2

Figure 2:
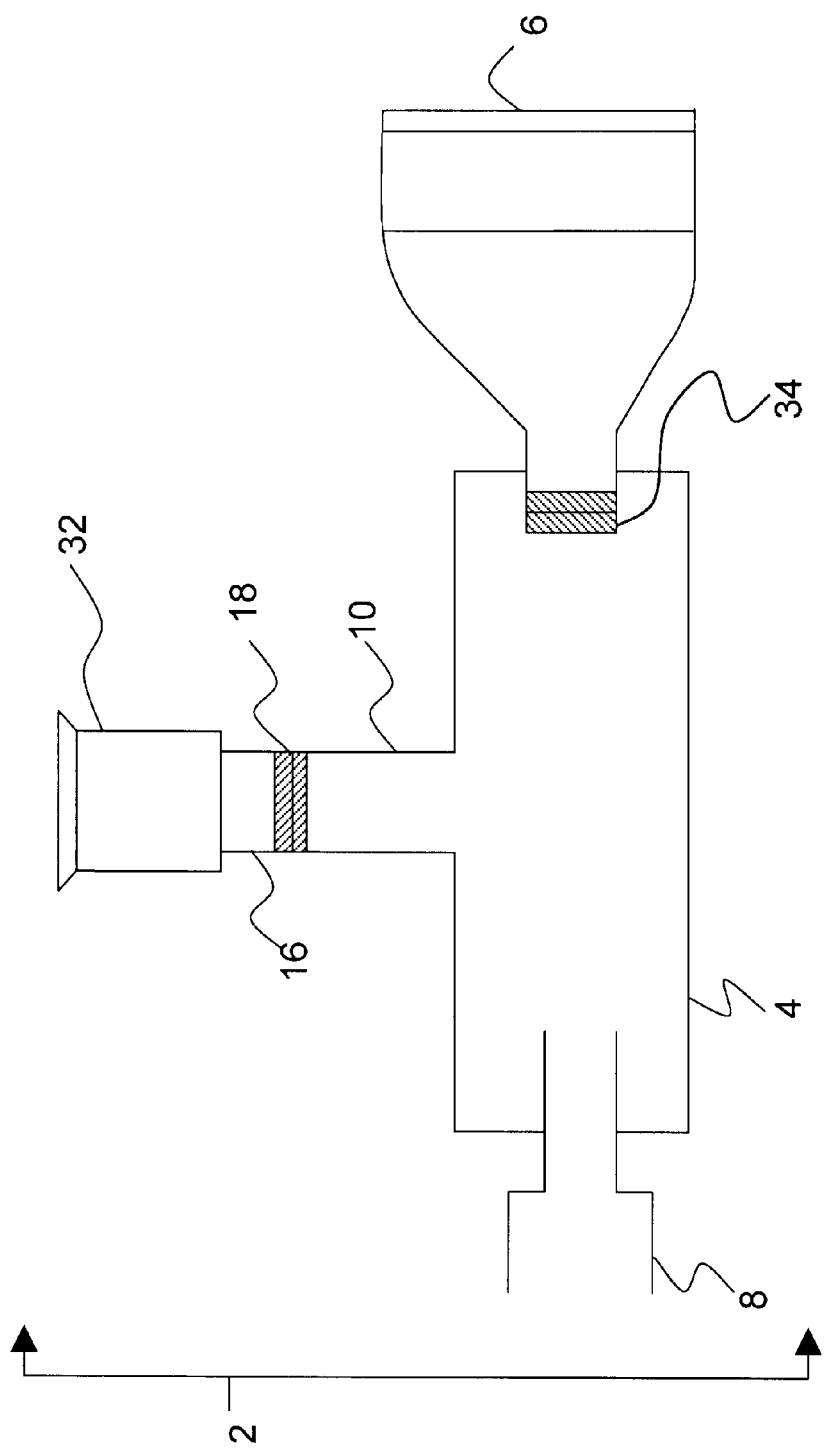
FIG. 2 is a sectional view of a further embodiment of the modular incentive inhaler device, wherein a single inhalation-driven incentive toy is positioned between the mask (6) and the linkable drug delivery device via a conduit.

An Incentive Inhaler Device Comprising an Inhalation-driven Incentive Toy Attached to the Connector or Spacer via a Conduit FIG. 2 illustrates a second embodiment of the invention comprising a incentive inhaler device (2) having a single inhalation-driven incentive toy unit (32) attached to the separator element (10) said separator element comprising an inhalation conduit (16) having a one-way valve (18) in sealing engagement therewith through which only inhaled air can pass.

In use, a metered dose of medicament is released into the connector (4) via a drug delivery device (not shown) that is releasably engaged in a sealing manner to the drug delivery device receiving means (8). The mask (6) is brought into contact with a patient's face and then the patient inhales. Alternatively, the patient may inhale simultaneously with bringing the mask (6) to his/her face. The device shown in FIG. 2 functions essentially in the same way as the device set forth in FIG. 1, however in the instant embodiment there is no mechanism for exhalation into the connector (4). To prevent exhaled air/medicament mixture from entering the connector (4), there is located between the junction of the mask (6) and the connector (4) a one-way valve (34), preferably a flap-type valve such as described in U.S. Pat. No. 4,470,412 and/or Australian Patent No. 620375, to release the expired air outside the entire device assembly.

Those skilled in the art will recognize that the connector (4) depicted in FIG. 2 may be integral with a spacer unit as hereinbefore defined, or function as a spacer unit as hereinbefore defined.

EXAMPLE 3

Figure 3:
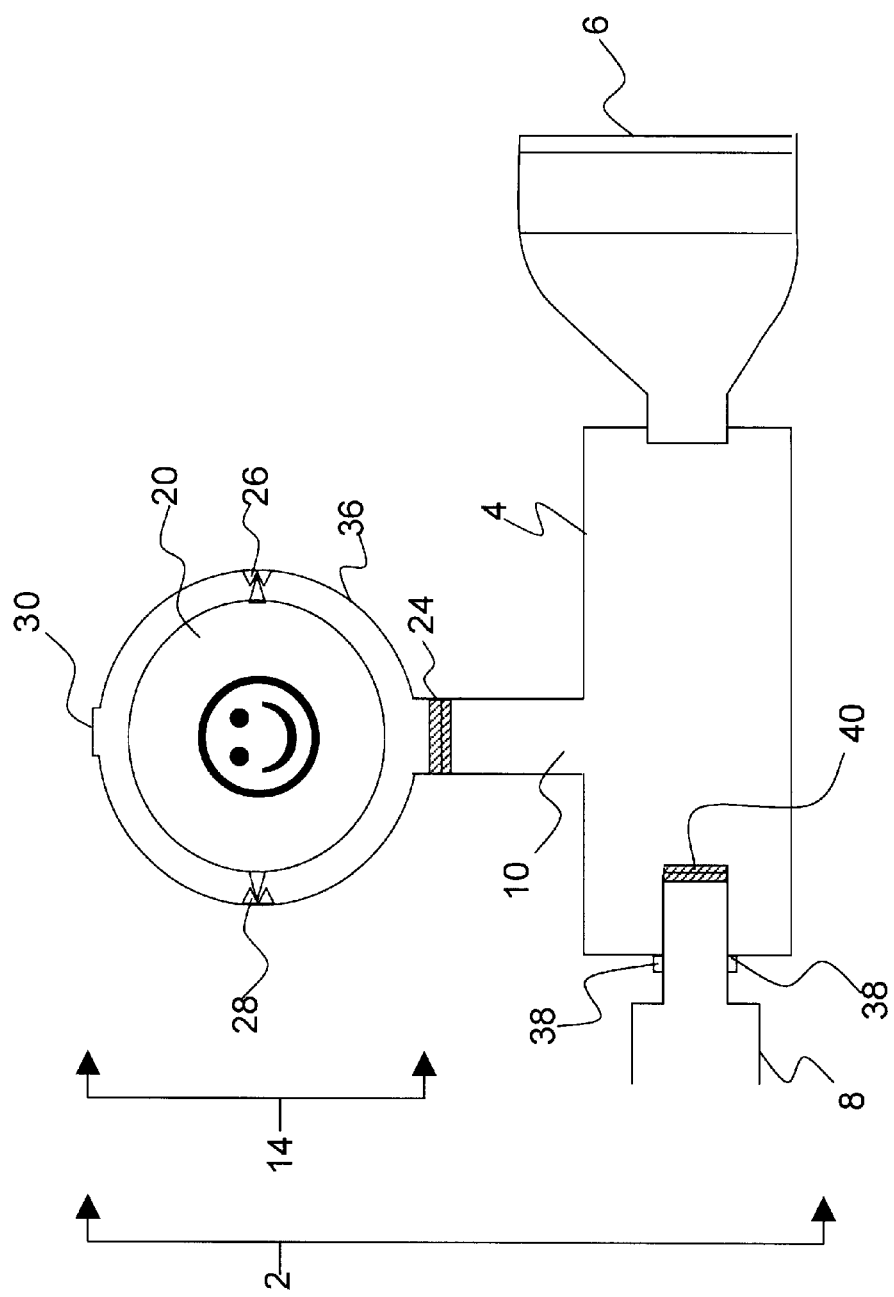
FIG. 3 is a sectional view of a further embodiment of the modular incentive inhaler device, wherein a single exhalation-driven incentive toy is positioned between the mask (6) and the linkable drug delivery device via a conduit.

An Incentive Inhaler Device Comprising an Exhalation-driven Incentive Toy Attached to the Connector or Spacer via a Conduit FIG. 3 illustrates a third embodiment of the incentive inhaler device of the invention (2) comprising a single exhalation-driven incentive toy unit (14) comprising a transparent orb (36) having an internal spinning disc (20) wherein said toy unit (14) is attached to the connector (4) via a separator element (10), said separator element including a one-way valve (24) that is activated by positive pressure within the separator element (10) such that only exhaled air can enter the toy unit (14).

In use, a metered dose of medicament is released into the spacer via a drug delivery device (not shown) that is sealably-engaged with the drug delivery receiving means (8). The mask (6) is brought into contact with a patient's face and then the patient inhales. Alternatively, the patient may inhale simultaneously with bringing the mask (6) to his/her face. As there is no inhalation-driven incentive toy unit attached to this device, the device is modified to provide a portal (38) juxtaposed to the receiving means (8) through which air may be inhaled into the connector (4). Anterior to the portal and positioned in one end of the drug delivery receiving means (8), there is a one-way valve (40) which allows medicament released from the drug delivery device into the connector (4), but prevents the flow of medicament and/or air/medicament mixture therefrom in the opposite direction.

During or prior to inhalation, medicament is released into the receiving means (8) from the drug delivery device, forcing open the one-way valve (40), thereby permitting entry of medicament into the connector (4). When a patient inhales, negative pressure is created in the connector (4), thereby opening the one-way valve (40). Air is also drawn into the connector (4) via the portal (38). As air enters the connector (4), it mixes with the medicament and the air/medicament mixture can be inhaled through the mask (6) into the patient's respiratory system.

To prevent medicament escaping through the portal (38) during inhalation or exhalation, there can be located in the portal (38) a one-way valve or similar device that closes when a positive pressure is applied to the space between the receiving means (8) and the one-way valve (40). In an alternative embodiment, the portal (38) may be formed as small holes that do not readily permit the escape or release of a large volume of a medicament in the period of time taken to administer a single dose of drug using the incentive inhaler device of the present invention. In a further embodiment, air enters the connector (4) directly, via the drug delivery device (not shown), thereby dispensing with the portal (38).

During exhalation, air mixed with residual medicament is blown into the connector (4) and passes into the separator element (10) and through the one-way valve (24) whereupon it enters the exhalation-driven incentive toy unit (14), exemplified herein as a spinning disc (20) contained within a transparent orb (36) in the identical arrangement to that shown in FIG. 1. Exhaled air/medicament mixture is prevented from escaping via the one-way valve (40) in the drug delivery receiving means (8). The illustrated device then functions in the same way as the embodiment illustrated in FIG. 1. In particular, a positive pressure is created in the connector, thereby forcing air/medicament mixture to enter the conduit of the of the separator element (10). Air/medicament mixture moves up the conduit of the separator element (10) passes through the second one-way valve (24) and into the exhalation-driven incentive toy unit (14), thereby activating movement of the spinning disc (20). As exhaled air/medicament mixture is blown into the unit (14), it is forced over the disc (20) causing it to spin around its mounts (26 and 28). The air/medicament mixture then passes out of the unit via an air release aperture (30).

Those skilled in the art will recognize that the connector (4) may be integral with a spacer and hereinbefore defined or function as a spacer unit as hereinbefore defined.

EXAMPLE 4

Figure 4:
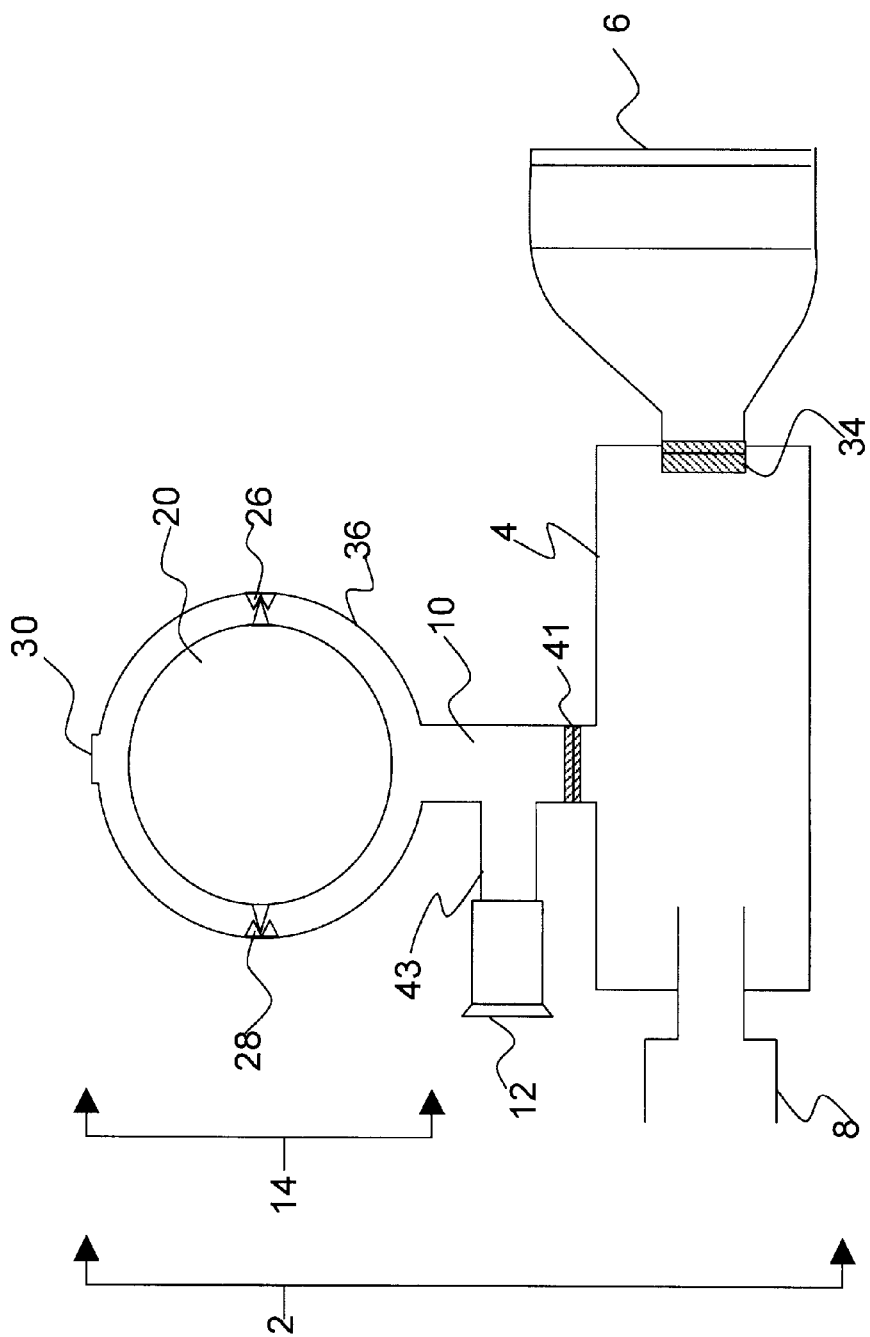
FIG. 4 is a sectional view of a further embodiment of the modular incentive inhaler device, wherein two inhalation-driven incentive toys are positioned between the mask (6) and the linkable drug delivery device via a conduit.

An Incentive Inhaler Device Comprising Dual Inhalation-driven Incentive Toys Attached to the Connector or Spacer via a Conduit FIG.4 illustrates a further embodiment of the incentive inhaler device (2) invention comprising dual exhalation-driven or dual inhalation-driven incentive toys in particular, a whistle (12) and a spinning disc unit (14) comprising a spinning disc (20) within a transparent orb (36). This device is substantially identical to that described in Example 1 however utilizes a separator element (10) comprising a three-way conduit (43) including one reversible one-way valve (41) placed nearer to the connector (4) such that toys 12 and 14 are driven by inhalation or exhalation depending upon the orientation of the valve (41).

In one embodiment a one-way valve (41), such as a butterfly valve, is provided in the conduit of the separator element (10), between the inhalation-driven toys (12 and 14) and the connector (4), which valve opens when a negative pressure is applied in the conduit and closes when a positive pressure is present in the connector (4).

During or prior to inhalation, medicament is released into the receiving means (8) from the drug delivery device, thereby permitting entry of medicament into the connector (4). When a patient inhales, negative pressure is created in the connector (4), thereby opening the one-way valve. Air/medicament mixture is then forced both through the whistle (12) causing a siren to sound, and over the disc (20) causing it to spin around its mounts (26 and 28).

During exhalation, air mixed with residual medicament is blown towards the connector (4) forcing the one-way valve (34) closed. Thus, one-way valve (34) blocks the entry of exhaled air into the connector during exhalation. The additional one-way valve (34) is of a construction known to those skilled in the art, such as a flap-type valve (U.S. Pat. No. 4,470,412 and/or Australian Patent No. 620375), is included in this embodiment of the present invention to provide for the release of exhaled air/medicament mixture to the outside of the entire device assembly.

While this embodiment is illustrated as a dual inhalation-driven incentive inhaler device, it will be appreciated that by reversing the one-way valve (41) (e.g. the butterfly valve) and removing the additional one-way valve (34)) (e.g. the flap-type valve), it is possible to convert the device to a dual exhalation-driven incentive inhaler device. In this embodiment, the whistle (12) is also reversed so that the siren sounds on exhalation, rather than on inhalation.

Those skilled in the art are aware that the connector (4) may be integral with a spacer as hereinbefore defined or function as a spacer unit as hereinbefore defined.

EXAMPLE 5

Figure 5:
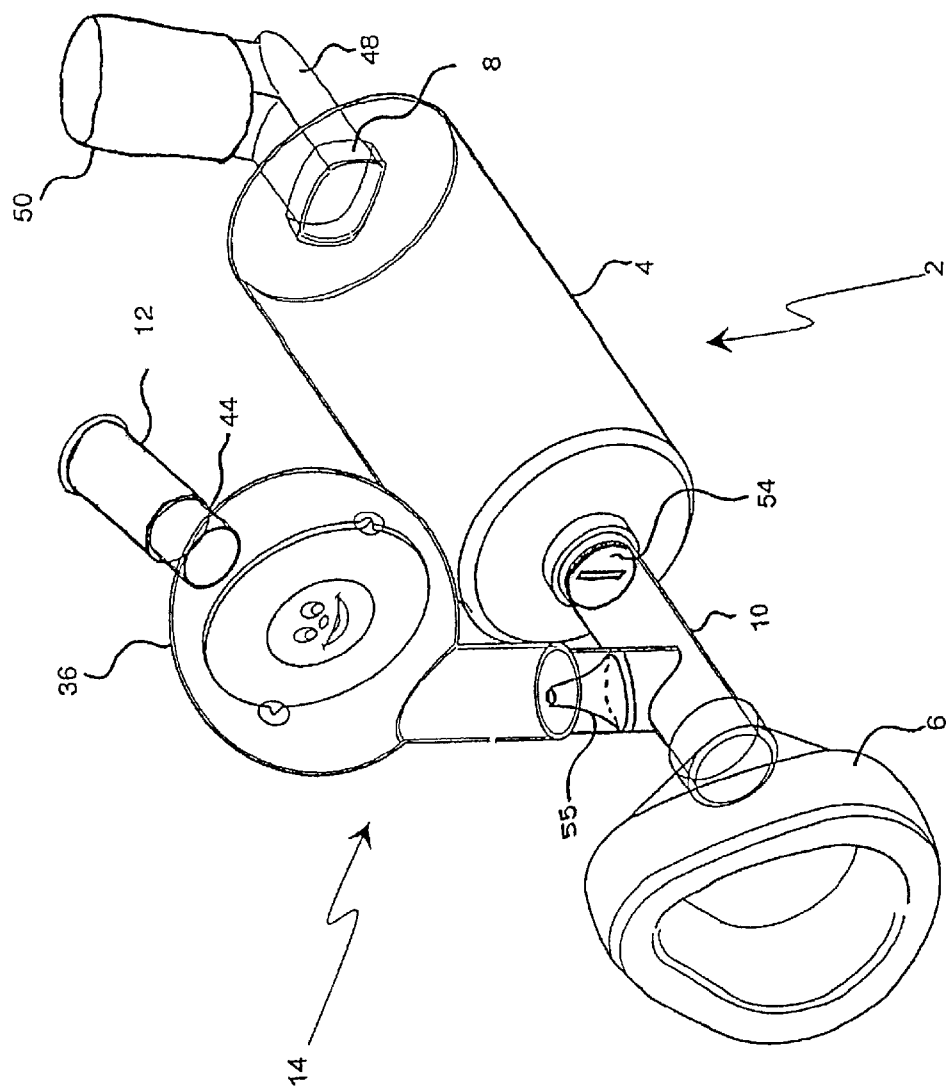
FIG. 5 is a sectional view of a further embodiment of the modular incentive inhaler device, wherein two exhalation-driven incentive toys are positioned between the mask (6) and the linkable drug delivery device via a conduit.

An incentive inhaler Device Comprising Inhalation-driven and Exhalation-driven Incentive Toys Attached to a Spacer via a Three-way Conduit FIG. 5 illustrates a further embodiment of the invention comprising an incentive inhaler device (2) with multiple inhalation-driven and exhalation-driven incentive toy units (12 and 14), wherein toy unit (14) consists of an exhalation-driven spinning disc within a transparent orb (36) and toy unit (12) consists of a reversible inhalation/exhalation-driven whistle or siren. Toy units 12 and 14 are attached in series to a separator element (10) comprising three-way conduit having a one-way valve (54) in sealing engagement with an inner wall thereof In particular, the transparent orb (36) has attached to it whistle unit (12). Whistle unit (12) is designed to allow for the bi-directional flow of air or air/medicament mixture, however only sounds a siren when air passes through in one direction.

Accordingly, in one arrangement, air passes through the whistle (12) on inhalation, causing the siren to sound. The inhaled air then passes through the transparent orb (36) however fails to activate the spinning disc therein. The whistle (12) is unidirectional, and, when configured in the opposite orientation, is activated on exhalation.

The connector (4) releasably engages the three-way conduit of the separator element (10) in a sealing manner. A metered dose of medicament is released into the connector (4) via a drug delivery device (48) that is releasably engaged in a sealing manner to the drug delivery device receiving means (8). The drug delivery device (48) shown in FIG. 5 is an asthma pump inhaler or MDI having an optional covering rubber seal (50) to prevent medicament leakage from the sides of the device after it is released into the connector (4). This seal, whilst not an essential feature of the present invention, can also improve the action of inhalation-driven toys, such as those illustrated in FIGS. 2 and 4.

The mask (6) is brought into contact with a patient's face and then the patient inhales. Alternatively, the patient may inhale simultaneously with bringing the mask (6) to his/her face. During inhalation, air is drawn into the incentive inhaler device (2) via the inhalation-driven incentive whistle (12). Depending upon the orientation of the whistle (12) a siren can sound as air is drawn through the whistle. Inhaled air passes through the orb (36) containing the spinning disc and enters the conduit of the toy unit (14) that is in sealable engagement with the three-way conduit of the separator element (10). The one-way valve (54) in the three way conduit of separator element (10) is, positioned in the adaptor end of said conduit that engages the connector (4), that prevents the reverse flow of inhaled air into the connector (4). Desirably the valve (54) is opened by negative pressure anterior thereto, such as in the mask (6) or the three-way conduit of the separator element (10), but seals when there is positive pressure in the mask (6) or the three-way conduit. The medicament is released into the connector (4) and, under a positive pressure that is produced within the connector (4), the one-way valve (54) opens to permit passage of the medicament into the three-way conduit of separator element. As air and medicament enter the three-way conduit of separator element (10) they are mixed and can be inhaled by the patient via the mask (6).

In a preferred form of the invention, the one-way valve may be adapted to be removed from the three-way conduit of separator element (10) to facilitate service or replacement of the valve should it cease working in a proper and efficient manner.

During the inhalation phase, the amount of medicament entering the exhalation-driven orb (36) containing the spinning disc is minimized because the direction of air flow is from the whistle (12) toward the three-way conduit of separator element (10).

Those skilled in the art will recognize that connector (4) may be integral with a spacer unit as hereinbefore defined or function as a spacer unit as hereinbefore defined.

During exhalation, air/medicament mixture is blown back into the three-way conduit of separator element (10) where with residual medicament that has not been inhaled. This creates a positive pressure in the three-way conduit of separator element (10), thereby forcing air/medicament mixture to enter the conduit of the toy unit (14). The air/medicament mixture is prevented from re-entering the connector (4) by the one-way valve (54) in the separator element (10). The adaptor end of the three-way conduit in separator element (10) that is in sealable engagement with the incentive toy unit (14) has a single passes over the exhalation-driven spinning disc of the transparent orb (36), thereby activating the spinning disc therein. The air/medicament mixture then passes out of the unit via an aperture in the whistle (12). Depending upon the orientation of the whistle [(42)](12), a siren can sound as air passes out of the device through the whistle.

EXAMPLE 6

An Incentive Inhaler Device for Use in Anaesthetic Applications

Figure 6:
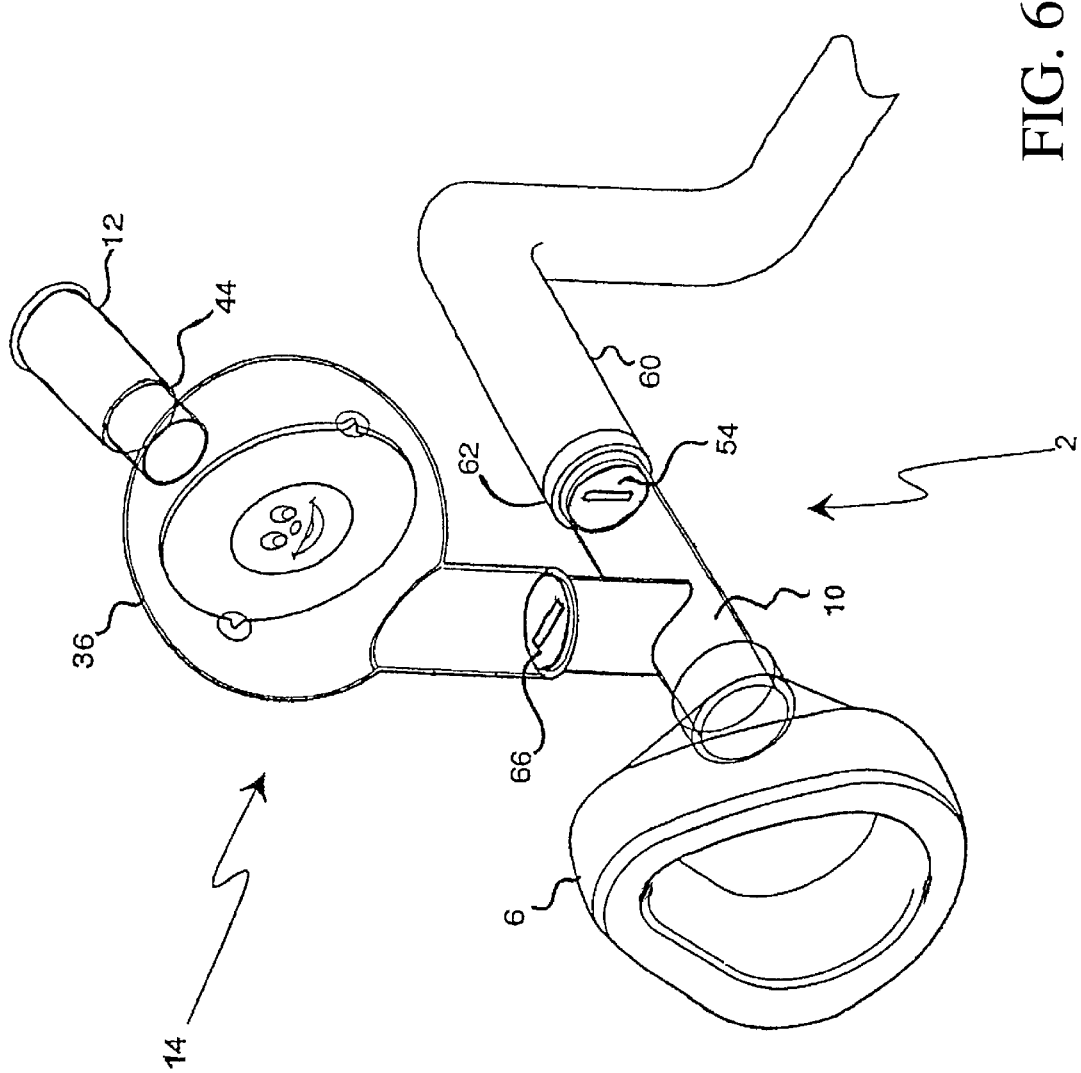
FIG. 6 is a sectional view of a further embodiment of the modular incentive inhaler device, wherein an inhalation-driven and an exhalation-driven incentive toy are positioned between the mask (6) and a drug delivery tube (60) via a conduit.
Figure 7:
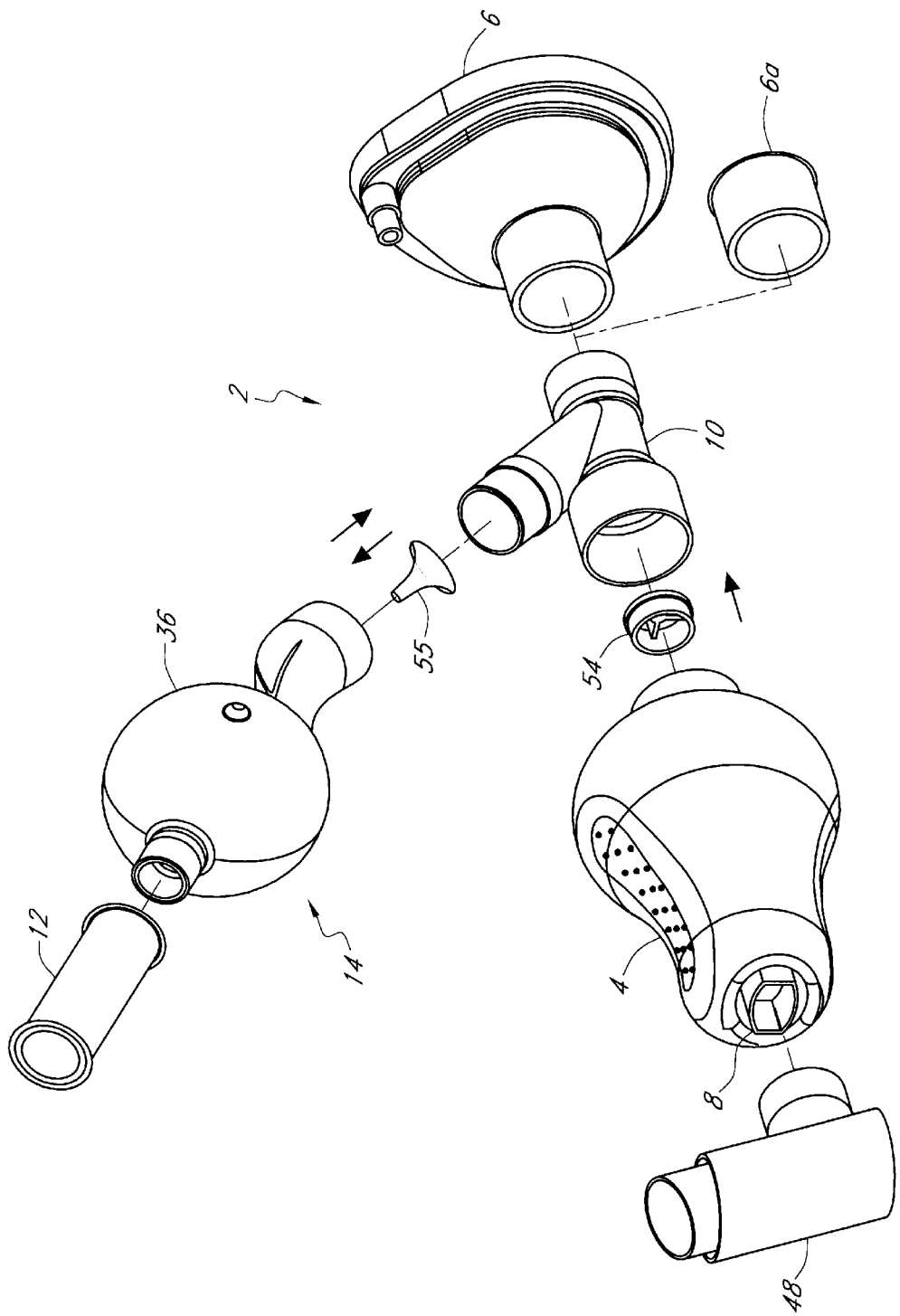
FIG. 7 is a view of a modification of the inhaler device of FIG. 5, showing the option of a mouth piece (6a), and a mask (6), and lacking rubber cap (50) present in FIG. 5. Other features are as indicated in the legend to FIG. 5. Broken lines indicate mode of assembly. The arrows indicate the direction of air flow.
Figure 8:
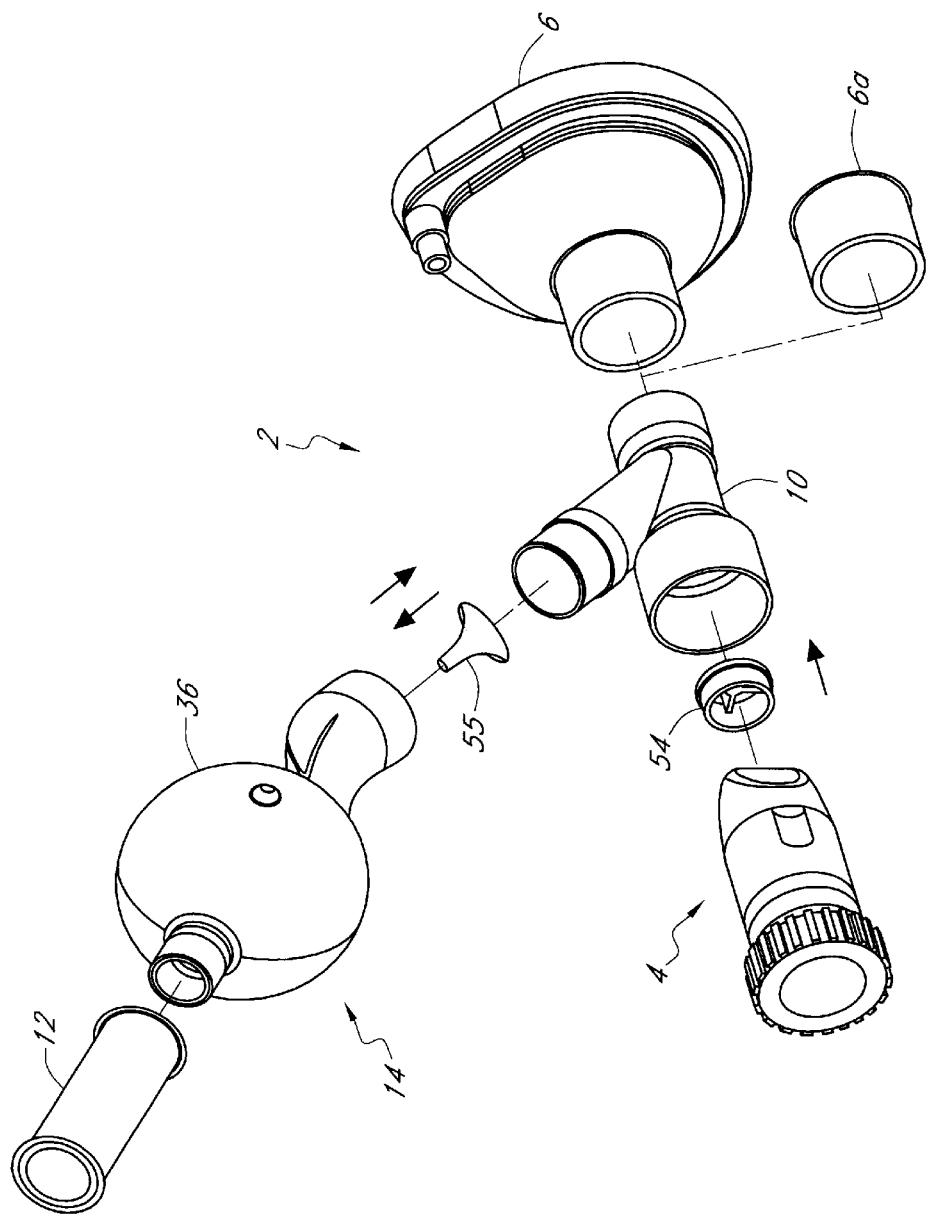
FIG. 8 is a view of a modification of the inhaler device of FIG. 5, showing the option of a mouth piece (6a) and mask (6), and including a connector (4) consisting of a dry powder inhalant dispenser in place of the conventional arrangement consisting of a spacer linked to an MDI as shown in FIG. 5. Broken lines indicate the mode of assembly. The arrows indicate the direction of air flow. Other features are as indicated in the legend to FIG. 5.

FIG. 6 illustrates a further embodiment of the invention comprising a incentive inhaler device (2) having attached thereto a connector comprising a drug delivery tube (60). The delivery tube (60) releasably and sealably engages a separator element (10) comprising a three-way conduit providing a continuous supply of drug to the mask (6). In this embodiment, an end of separator element (10) is adapted to engage directly to the delivery tube. Thus the receiving means is provided by one end of the drug delivery tube (60). A clamp (62) seals the tube to the three-way conduit of the separator element (10), ensuring sealing engagement between the tube and the conduit. At the junction between the delivery tube (60) and the three-way conduit of the separator element (10) is a one-way valve (54) that opens when negative pressure is applied from within the separator element (10). When the valve opens, anaesthetic passes from the delivery tube (60) into the separator element (10). To prevent this fluid escaping from the separator element (10) prior to inhalation by the patient, there is a further one-way valve (66) located in an adaptor end of said separator element (10) that is in engagement with the conduit of the incentive toy module (14). The one-way valve (66) opens when a positive pressure is applied from within the separator element (10), and, preferably, only during the exhalation phase of breathing, when anaesthetic mixed with air is exhaled into the three-way conduit of the separator (10). More preferably, the pressure required to open valve (66) correlates with the pressure created by inhalation and exhalation of anaesthetic through the incentive inhaler device.

In use, the mask (6) is brought into contact with a patient's face and then the patient inhales anaesthetic directly from the drug delivery device (not shown) via the drug delivery tube (60) and separator element (10). Alternatively, the patient may inhale simultaneously with bringing the mask (6) to his/her face.

During exhalation, air/anaesthetic mixture is blown back into the separator element (10) where it mixes with residual anaesthetic that has not been inhaled. This creates a positive pressure in the separator element (10), thereby forcing the one-way valve (66) open, to facilitate passage of air/anaesthetic mixture to enter the conduit of toy unit (14). The air/anaesthetic mixture is prevented from re-entering the drug delivery tube (60) by the one-way valve (54). The air/anaesthetic mixture passes through a transparent orb (36) and over the spinning disc located therein of the exhalation-driven incentive toy unit, thereby activating the spinning disc. The air/medicament mixture then passes out of the unit via an aperture in the whistle (12). Depending upon the orientation of the whistle (12), a siren can sound as air passes out of the device through the whistle.

While this embodiment of the present invention provides for exhaled anaesthetic to be released to the atmosphere, the second exhalation-driven incentive toy unit (12) may be adapted to sealingly engage (preferably in a releasable manner) a scavenging system exhaust tube. In such an embodiment exhaled anaesthetic gases may be collected and stored without release into the treatment environment.

What is claimed is:

1. An incentive inhaler device, comprising:
    an inhalation device comprising a respiration device and a connector that is linkable to a drug delivery device such that there is a main inspiration flow of a medicament from said drug delivery device into said respiration device via said connector during inspiration by a subject through said respiration device;
    at least one incentive toy coupled to the inhalation device, the toy being driven by inhaled or exhaled air passing over said toy or through said toy, wherein said toy has a visible characteristic or an audible characteristic; and
    a separator element positioned so as to separate said toy from said main inspiration flow of a medicament and provide a separate air flow passage over or through said toy from or to outside said main inspiration flow, wherein said separator element includes an integer selected from the group consisting of: a valve, a filter, and a baffle.

2. The incentive inhaler device of claim 1, wherein the separator includes at least one one-way valve.

3. The incentive inhaler device of claim 1, wherein the connector comprises:
    an aperture at one end to sealably-engage the drug delivery device such that minimum leakage of the medicament occurs between the connector and the drug delivery device linked thereto; and
    an end segment to releasably- and sealably-engage said connector to the respiration device.

4. The incentive inhaler device of claim 1, comprising at least one of an external visible incentive toy, an audible inhalation-driven incentive toy, and an audible exhalation-driven incentive toy.

5. The incentive inhaler device of claim 1, comprising an inhalation-driven incentive toy and an exhalation-driven incentive toy.

6. The incentive inhaler device of claim 1, comprising two incentive toys which are linked in series.

7. The incentive inhaler device of claim 1, wherein at least one incentive toy comprises a colored spinning disc.

8. The incentive inhaler device of claim 1, wherein at least one incentive toy comprises an acoustic device, the acoustic device being selected from a group consisting of a bi-directional siren, a bi-directional whistle, a uni-directional siren, and a uni-directional whistle.

9. The incentive inhaler device of claim 8, wherein the acoustic device is unidirectional and reversible attached such that in a first position sound is made upon inhalation and in a second position sound is made upon exhalation.

10. The incentive inhaler device of claim 1, wherein the valve is a one-way valve positioned within a conduit of the separator element that provides for an attachment of the incentive toy in sealable engagement with an interior wall of said conduit.

11. The incentive inhaler device of claim 10, wherein the conduit comprises at least three adaptor ends for connection of the respiration device, the connector and at least one incentive toy, and wherein at least one valve is positioned within the conduit in sealable engagement with the interior wall thereof at least one of said adaptor ends.

12. The incentive inhaler device of claim 11, wherein the one-way valve is positioned within the conduit in sealable engagement therewith and at an adaptor end that connects to the connector, such that a medicament can be drawn into the respiration device from the drug delivery device but not in an opposite direction.

13. The incentive inhaler device of claim 10, wherein the incentive toy is inhalation-driven, and the one-way valve is positioned within the conduit in sealable engagement therewith and at one end of said conduit that connects to said incentive toy, such that air can be drawn via said incentive toy and into the respiration device via the conduit but not in an opposite direction.

14. The incentive inhaler device of claim 10, wherein the incentive toy is exhalation-driven, and the one-way valve positioned within the conduit in sealable engagement therewith and at one end of said conduit that connects to said incentive toy, such that an exhaled air/medicament mixture can pass via said incentive toy from the respiration device but not in an opposite direction.

15. The incentive inhaler device of claim 10, further comprising at least one venturi comprising a frustoconical portion tapered at one end, said venturi being positioned: (i) coaxially within the conduit such that a circumference of an outer wall of said venturi is in sealable engagement with a circumference of the interior wall of the conduit; and (ii) sufficiently near to an end of said conduit that connects to the incentive toy such that a velocity of air is increased when it passes through said venturi thereby increasing a velocity of air passing from said venturi over or through said toy.

16. The incentive inhaler device of claim 10, further comprising a spacer unit positioned between the respiration device and the connector.

17. The incentive inhaler device of claim 1, wherein the separator element is positioned in sealable engagement with both the respiration device and the connector.

18. The incentive inhaler device of claim 17, wherein the connector comprises:
    an aperture at one end to sealably-engage the drug delivery device thereby minimizing leakage of a medicament between the connector and the drug delivery device linked thereto; and
    an end segment to releasably- and sealably-engage said connector to the separator element.

19. The incentive inhaler device of claim 18, wherein the end segment includes a snap-lock.

20. The incentive inhaler device of claim 1, further comprising a spacer unit positioned between the respiration device and the connector.

21. A connector for use with the incentive inhaler device of claim 1, comprising:
    a drug delivery receiving means comprising an aperture at one end to sealably-engage the drug delivery device such that minimum leakage of a medicament occurs between the connector and the drug delivery device linked thereto; and an end segment to releasably- and sealably-engage said connector to a respiration device with which said connector is associated in the incentive inhaler device.

22. The connector of claim 21, wherein the drug delivery receiving means is flexible in order to conform to fit a variety of drug delivery ports.

23. The incentive inhaler device of claim 1 wherein the separator element is connected to the respiration device.

24. The incentive inhaler device of claim 1 wherein the separator element is connected to the connector.

25. The incentive inhaler device of claim 1 wherein the respiration device is a mouthpiece or mask.

26. The incentive inhaler of claim 1 wherein the separator element directs inhaled air to said toy.

27. The incentive inhaler of claim 1 wherein the separator element directs exhaled air to said toy.

28. An incentive inhaler device for administering an anaesthetic, comprising:
    a mask;
    a drug delivery tube that is linkable to a drug delivery device such that during inspiration there is a main inspiration flow of anaesthetic from the drug delivery device to the mask via said drug delivery tube;
    at least one incentive toy driven by exhaled air passing over said toy or through said toy wherein said toy has a visible characteristic or an audible characteristic; and
    a separator element comprising a conduit, wherein said conduit comprises three adaptor ends that are connected separately to said mask, said drug delivery tube and said incentive toy, and wherein said conduit comprises a one-way valve in sealing engagement with an interior wall of an adaptor end juxtaposed to the incentive toy to prevent a flow of inhaled air from the incentive toy to the mask and to separate said toy from said main inspiration flow of anaesthetic.

29. The incentive inhaler device of claim 28, further comprising a second one-way valve in sealing engagement with an interior wall of an adaptor juxtaposed to the drug delivery tube to prevent flow of exhaled air to the drug delivery tube.

30. The incentive inhaler device of claim 28, further comprising at least one venturi comprising a frustoconical portion tapered at one end, said venturi being positioned: (i) coaxially within the conduit such that a circumference of an outer wall of said venturi is in sealable engagement with a circumference of the interior wall of the adaptor end of the conduit juxtaposed the incentive toy; and (ii) sufficiently near to the incentive toy such that a velocity of air passing through said venturi is increased thereby increasing a velocity of air passing from said venturi over or through said toy.

31. The incentive inhaler device of claim 23, wherein the incentive toy comprises an exhalation-driven whistle and an exhalation-driven spinning disc.

32. The incentive inhaler device of claim 28, further comprising a scavenger pipe in engagement with the exhalation-driven incentive toy, such that exhaled air passing via said incentive toy is collected in a scavenger system comprising the scavenger pipe.

33. A method of operating an incentive inhaler device to administer an inhalable medicament to a child, comprising:
    (a) providing an incentive inhaler device comprising:
        (i) an inhalation device comprising a respiration device and a connector that is linkable to a drug delivery device such that there is a main inspiration flow of a medicament from said drug delivery device into said respiration device via said connector during inspiration by a child;
        (ii) at least one incentive toy coupled to the inhalation device, being driven by inhaled or exhaled air passing over said toy or through said toy, wherein said toy has a visible characteristic or an audible characteristic; and
        (iii) at least one separator element positioned so as to separate said toy from said main inspiration flow of a medicament and provide a separate air flow passage over or through said toy from or to outside said main inspiration flow wherein said separator element includes an integer selected from the group consisting of: a valve, a filter and a baffle;

(b) bringing the respiration device in contact with a child's face; and (c) causing a child to inhale through the respiration device or exhale into the respiration device thereby activating said toy.

34. The method of claim 23 further comprising selecting an inhalable medicament from the group consisting of an anti-inflammatory compound, a natural steroid, a synthetic steroid, a bronchodilator, a vasodilator, a naturopathic medicine, a homeopathic medicine, an antihistamine, an antibiotic, a cough mixture, a tranquilizer, an anaesthetic, a therapeutic drug including at least one of nitrous oxide, oxygen, and air, an adrenergic receptor agonist, an adrenergic receptor antagonist, a beta-agonist, and a beta-blocker.

35. A method of operating an incentive inhaler device to administer an anaesthetic to a child comprising:
   (a) providing an incentive inhaler device comprising:
      (i) a mask;
      (ii) a drug delivery tube that is linkable to a drug delivery device such that during inspiration there is a main inspiration flow of anaesthetic from the drug delivery device to the mask via said drug delivery tube;
      (iii) at least one incentive toy driven by exhaled air passing over said toy or through said toy, wherein said toy has a visible characteristic or an audible characteristic; and
      (iv) a separator element comprising a conduit, wherein said conduit comprises three adaptor ends that are connected separately to said mask, said drug delivery tube and said incentive toy and wherein said conduit comprises a one-way valve in sealing engagement with an interior wall of adaptor end juxtaposed to said incentive toy to prevent a flow of inhaled air from the incentive toy to the mask and to separate said toy from said main inspiration flow of anaesthetic;
   (b) bringing the mask in contact with a child's face;
   (c) causing said child to exhale into the mask thereby activating the incentive toy; and
   (d) optionally, exhausting the exhaled air into a scavenger system.

36. An incentive inhaler device comprising:
   (i) an inhalation device comprising a respiration device and a connector that is linkable to a drug delivery device such that there is a main inspiration flow of a medicament from said drug delivery device into said respiration device via said connector during inhalation by a subject through said respiration device;
   (ii) two incentive toys coupled to the inhalation device, the toys having an audible characteristic or a visible characteristic, wherein said toys are driven by inhaled air and/or exhaled air passing over them or through them; and
   (iii) a separator element consisting of a three-way conduit comprising:
      (a) an adaptor end for operable attachment of the incentive toys to the inhalation device;
      (b) a venturi comprising a frustoconical portion tapered at one end, said venturi being positioned: (i) coaxially within the conduit such that a circumference of an outer wall of said venturi is in sealable engagement with a circumference of an interior wall of said separator element; and (ii) sufficiently near to said adaptor end such that a velocity of air passing through said venturi is increased thereby increasing a velocity of air passing from said venturi over or through said incentive toys attached to said adaptor end; and
      (c) a one-way valve in sealing engagement with an interior wall of an adaptor end juxtaposed said drug delivery device or said connector to ensure a directional flow of air, wherein said separator element is positioned so as to separate said toys from said main inspiration flow of a medicament.

37. The incentive inhaler device of claim 36 wherein the separator element is connected to the respiration device.

38. The incentive inhaler device of claim 36 wherein the separator element is connected to the connector.

39. The incentive inhaler device of claim 36 further comprising a spacer positioned between the respiration device and the connector.

40. The incentive inhaler device of claim 36 wherein the incentive toys consist of a whistle and a spinning disc.

41. The incentive inhaler device of claim 36 wherein the respiration device is a mouthpiece or mask.

42. A method of operating an incentive inhaler device for administering a medicament to a child comprising:
   (a) providing an incentive inhaler device comprising:
      (i) an inhalation device comprising a respiration device and a connector that is linkable to a drug delivery device such that there is a main inspiration flow of a medicament from said drug delivery device into said respiration device via said connector during inhalation by a child through said respiration device;
      (ii) two incentive toys coupled to the inhalation device, the toys having an audible characteristic or a visible characteristic, wherein said toys are driven by inhaled air and/or exhaled air passing over them or through them;
      (iii) a separator element consisting of a three-way conduit comprising:
         (a) an adaptor end for operable attachment of the incentive toys to the inhalation device;
         (b) a venturi comprising a frustoconical portion tapered at one end, said venturi being positioned:
            (i) coaxially within said conduit such that a circumference of an outer wall of said venturi is in sealable engagement with a circumference of an interior wall of said separator element; and (ii) sufficiently near to said adaptor end such that a velocity of air passing through said venturi is increased thereby increasing a velocity of air passing from said venturi over or through said incentive toys attached to said adaptor end; and
            (c) a one-way valve in sealing engagement with an interior wall of an adaptor end juxtaposed said drug delivery device or said connector to ensure a directional flow of air, wherein said separator element is positioned so as to separate said toys from said main inspiration flow of a medicament;
   (b) bringing the respiration device in contact with a child's face; and
   (c) causing said child to inhale and exhale into the respiration device thereby activating said toys.

43. The method of claim 42 further comprising selecting an inhalable medicament from the group consisting of an anti-inflammatory compound, a natural steroid, a synthetic steroid, a bronchodilator, a vasodilator, a naturopathic medicine, a homeopathic medicine, an antihistamine, an antibiotic, a cough mixture, a tranquilizer, an anaesthetic, a therapeutic drug including at least one of nitrous oxide, oxygen, and air, an adrenergic receptor agonist, an adrenergic receptor antagonist, a beta-agonist, and a beta-blocker.

44. An incentive inhaler device comprising:
(i) an inhalation device comprising a respiration device and a connector that is linkable to a drug delivery device such that there is a main inspiration flow of a medicament from said drug delivery device into said respiration device via said connector during inhalation by a subject through said respiration device;
(ii) a toy unit comprising two incentive toys coupled to said inhalation device wherein one toy has an audible characteristic activated by air passing over or through it and wherein one toy has a visible characteristic activated by air passing over or through it;
(iii) a separator element comprising a three-way conduit operably connected at one end to said respiration device and at another end to said connector, said conduit including an adaptor end for operable attachment of the toy unit to the inhalation device, said adaptor end including a one-way valve in sealing engagement with an interior wall of said adaptor end juxtaposed to the toy unit to ensure a directional flow of inhaled or exhaled air over or through said toy unit, said separator element positioned so as to separate said toy unit from said main inspiration flow of a medicament.

45. The incentive inhaler device of claim 44 wherein the toys are driven by exhaled air.

46. The incentive inhaler device of claim 44 wherein the toys are driven by inhaled air.

47. The incentive inhaler device of claim 44 wherein the separator element is connected to the respiration device.

48. The incentive inhaler device of claim 44 wherein the separator element is connected to the connector.

49. The incentive inhaler device of claim 44 further comprising a spacer positioned between the respiration device and the connector.

50. The incentive inhaler device according to claim 44 further comprising at least one venturi comprising a frustoconical portion tapered at one end, said venturi being positioned: (i) coaxially within the conduit such that a circumference of an outer wall of said venturi is in sealable engagement with a circumference of an interior wall of said conduit; and (ii) sufficiently near to said adaptor end of said conduit such that a velocity of air passing through said venturi is increased thereby increasing a velocity of air passing from said venturi over or through said incentive toys attached to said adaptor end.

51. The incentive inhaler device of claim 44 wherein the incentive toys consist of a whistle and a spinning disc.

52. The incentive inhaler device of claim 44 wherein the respiration device is a mouthpiece or mask.

53. A method of operating an incentive inhaler device for administering a medicament to a child comprising:
(a) providing an incentive inhaler device comprising:
(i) an inhalation device comprising a respiration device and a connector that is linkable to a drug delivery device such that there is a main inspiration flow of a medicament from said drug delivery device into said respiration device via said connector during inhalation by a child through said respiration device;
(ii) a toy unit comprising two incentive toys coupled to said inhalation device wherein one toy has an audible characteristic activated by air passing over or through it and wherein one toy has a visible characteristic activated by air passing over or through it;
(iii) a separator element comprising a three-way conduit operably connected at one end to said respiration device and at another end to said connector, said conduit including an adaptor end for operable attachment of the toy unit to the inhalation device, said adaptor end including a one-way valve in sealing engagement with an interior wall of said adaptor end juxtaposed to the toy unit to ensure a directional flow of inhaled or exhaled air over or through said toy unit, said separator element positioned so as to separate said toy unit from said main inspiration flow of a medicament;
(b) bringing the respiration device in contact with a child's face; and
(c) causing a child to inhale or exhale to thereby activate said toys.

54. The method of claim 53 further comprising selecting an inhalable medicament from the group consisting of an anti-inflammatory compound, a natural steroid, a synthetic steroid, a bronchodilator, a vasodilator, a naturopathic medicine, a homeopathic medicine, an antihistamine, an antibiotic, a cough mixture, a tranquilizer, an anaesthetic, a therapeutic drug including at least one of nitrous oxide, oxygen, and air, an adrenergic receptor agonist, an adrenergic receptor antagonist, a beta-agonist, and a beta-blocker.

55. A separator element for connecting an incentive toy to an inhalation device having a respiration device and a connector that is linkable to a drug delivery device such that there is a main inspiration flow of a medicament from said drug delivery device into said respiration device via said connector during inspiration by a subject through said respiration device, the toy being driven by inhaled or exhaled air passing over said toy or through said toy, said separator element comprising a three-way conduit having a first end for connection to said respiration device, a second end for connection to said connector and an adaptor end for connection to said incentive toy, said separator element including a one-way valve in sealable engagement with an interior wall thereof to ensure a directional flow of inhaled or exhaled air over or through said toy, said separator element separating said toy from said main inspiration flow of a medicament.

56. The separator element as claimed in claim 55 wherein said one-way valve is position in said adaptor in sealing engagement with an interior wall of said adaptor end.

* * * * *